United States Patent [19]
Carr et al.

[11] Patent Number: 5,141,634
[45] Date of Patent: Aug. 25, 1992

[54] HIGH STABILITY POROUS ZIRCONIUM OXIDE SPHERULES

[75] Inventors: Peter W. Carr, Minneapolis; Eric F. Funkenbusch, White Bear Lake; Martin P. Rigney, Roseville; Patrick L. Coleman, Minneapolis; Douglas A. Hanggi, St. Paul; Wes A. Schafer, Minneapolis, all of Minn.

[73] Assignee: Regents of the University of Minnesota, Minneapolis, Minn.

[21] Appl. No.: 654,312

[22] Filed: Feb. 12, 1991

Related U.S. Application Data

[60] Division of Ser. No. 420,150, Oct. 11, 1989, Pat. No. 5,015,373, which is a continuation-in-part of Ser. No. 151,819, Feb. 3, 1988, abandoned.

[51] Int. Cl.⁵ .......................................... B01D 15/08
[52] U.S. Cl. ............................. 210/198.2; 210/502.1; 210/635; 210/656; 502/400
[58] Field of Search ................ 210/635, 656, 198.2, 210/502.1; 502/400, 439

[56] References Cited

U.S. PATENT DOCUMENTS

| | | | |
|---|---|---|---|
| 2,979,374 | 4/1961 | Drake et al. | 8/120 |
| 3,556,945 | 1/1971 | Messing | 195/63 |
| 3,782,075 | 1/1974 | Kirkland | 55/67 |
| 3,783,101 | 1/1974 | Tomb | 195/63 |
| 3,841,971 | 10/1974 | Messing | 195/63 |
| 3,850,751 | 11/1974 | Messing | 195/63 |
| 3,855,172 | 12/1974 | Iler et al. | 260/39 R |
| 3,862,908 | 1/1975 | Fitch et al. | 252/301.15 |
| 3,892,580 | 7/1975 | Messing | 106/41 |
| 3,892,678 | 7/1975 | Halasz et al. | 252/426 |
| 3,910,851 | 10/1975 | Messing | 252/455 R |
| 3,912,593 | 10/1975 | Barker et al. | 195/57 |
| 3,920,865 | 11/1975 | Laufer et al. | 427/220 |
| 3,956,179 | 5/1976 | Sebestian et al. | 252/430 |
| 3,960,762 | 6/1976 | Kroebel et al. | 252/426 |
| 4,010,242 | 3/1977 | Iler et al. | 423/335 |
| 4,138,336 | 2/1991 | Mendel et al. | 210/198.2 |
| 4,209,554 | 6/1980 | Traynor et al. | 427/230 |
| 4,298,500 | 11/1981 | Abbott | 252/428 |
| 4,330,440 | 5/1982 | Ayers et al. | 525/54.31 |
| 4,334,972 | 6/1982 | Soderberg | 204/180 R |
| 4,376,064 | 3/1983 | Hoff et al. | 252/429 B |
| 4,386,010 | 5/1983 | Hildebrandt | 252/428 |
| 4,389,385 | 6/1983 | Ramsay | 423/338 |
| 4,517,241 | 5/1985 | Alpert | 428/332 |
| 4,520,122 | 5/1985 | Arena | 502/152 |
| 4,544,485 | 10/1985 | Pinkerton et al. | 210/502.1 |
| 4,600,646 | 7/1986 | Stout | 428/405 |
| 4,648,975 | 3/1987 | Barkatt et al. | 210/656 |
| 4,673,734 | 6/1987 | Tayot et al. | 530/364 |
| 4,699,717 | 10/1987 | Riesner et al. | 210/635 |
| 4,871,711 | 10/1989 | Martin | 210/656 |

FOREIGN PATENT DOCUMENTS

| | | | |
|---|---|---|---|
| 169245 | 5/1977 | Czechoslovakia | 210/198.2 |
| 0162716 | 10/1985 | European Pat. Off. | 210/198.2 |
| 0216730 | 4/1987 | European Pat. Off. | 210/198.2 |
| 0273756 | 7/1988 | European Pat. Off. | 210/198.2 |
| 0280673 | 8/1988 | European Pat. Off. | 210/198.2 |
| 3440018 | 3/1986 | Fed. Rep. of Germany | 210/198.2 |
| 63-123817 | 5/1988 | Japan | 210/198.2 |

OTHER PUBLICATIONS

Alberti et al., *J. Inorg. Nucl. Chem.*, 40, 1113–1117 (1978).
Alberti et al., *J. Chromatography*, 180, 45–51 (1979).
Amphlett et al., *Chemistry and Industry*, 1314–1315 (Nov. 10, 1956).
Amphlett et al., *J. Inorg. Nucl. Chem.*, 6, 220–235 and 236–245 (1958).

(List continued on next page.)

Primary Examiner—Ernest G. Therkorn
Attorney, Agent, or Firm—Merchant, Gould, Smith, Edell, Welter & Schmidt

[57] ABSTRACT

The present invention provides a stable stationary phase for chromatography which comprises porous $ZrO_2$ spherules coated with a cross-linked polymer coating wherein said coated spherules have a pore size from about 20–500 Å and a particle diameter range of about 0.5–500 microns, and are stable in basic media to pHs of up to about 14.

11 Claims, 4 Drawing Sheets

30 MINUTE GRADIENT PROGRAM FROM 0.05 M PO₄ TO 0.5 M PO₄ (pH=7.0)

OTHER PUBLICATIONS

Baetsle et al., *J. Inorg. Nucl. Chem.*, 21, 124–132 and 133–140 (1961).

Barth et al., *Analytical Chemistry*, 60, 387R, 411R–413R, 429R–430R (1988).

Bien-Vogelsang et al., *Chromatographia*, 19, 170–176 (1984).

Clearfield et al., "New Inorganic Ion Exchangers", in *Ion Exchange and Solvent Extraction*, 5, Chapter 1, 1–61 and 104–120 (1973).

Figge et al., *J. Chromatography*, 351, 393–408 (1986).

Ghaemi et al., *J. Chromatography*, 174, 51–59 (1979).

Knox et al., *European Chromatography News*, 1, 12–17 (1987).

Kolla et al., *Chromatographia*, 23, 465–472 (1987).

Kraus et al., *Nature*, 1128–1129 (Jun. 16, 1956).

Marsh et al., *Biotechnology and Bioengineering*, XVIII, 349–362 (1976).

Maya et al., *J. Chromatography*, 190, 145–149 (1980).

McDonald et al., "Strategies for Successful Preparative Liquid Chromatography", in *Preparative Liquid Chromatography, J. Chromatography Library*, 38, 1, 6, 26–31, 62–64 (1987).

Schomburg et al., *Chromatographia*, 18, 265–274 (1984).

Schomburg et al., *J. Chromatography*, 282, 27–39 (1983).

Schomburg, *LC-GC*, 6, 36 (1988).

Stout et al., *J. Chromatography*, 326, 63–78 (1985).

ES Industries, "Application News ($\gamma$RP-1 HPLC Column and Comparison of the Chromegabond $\gamma$RP-1 and $\gamma$C18 Phases)" (Mar. 1987).

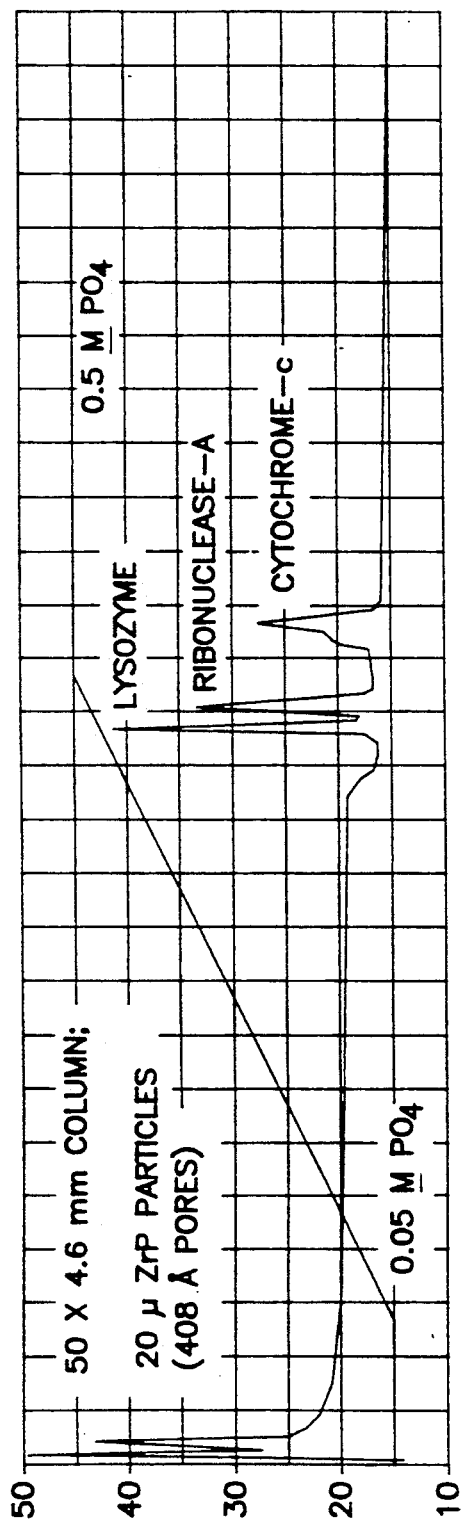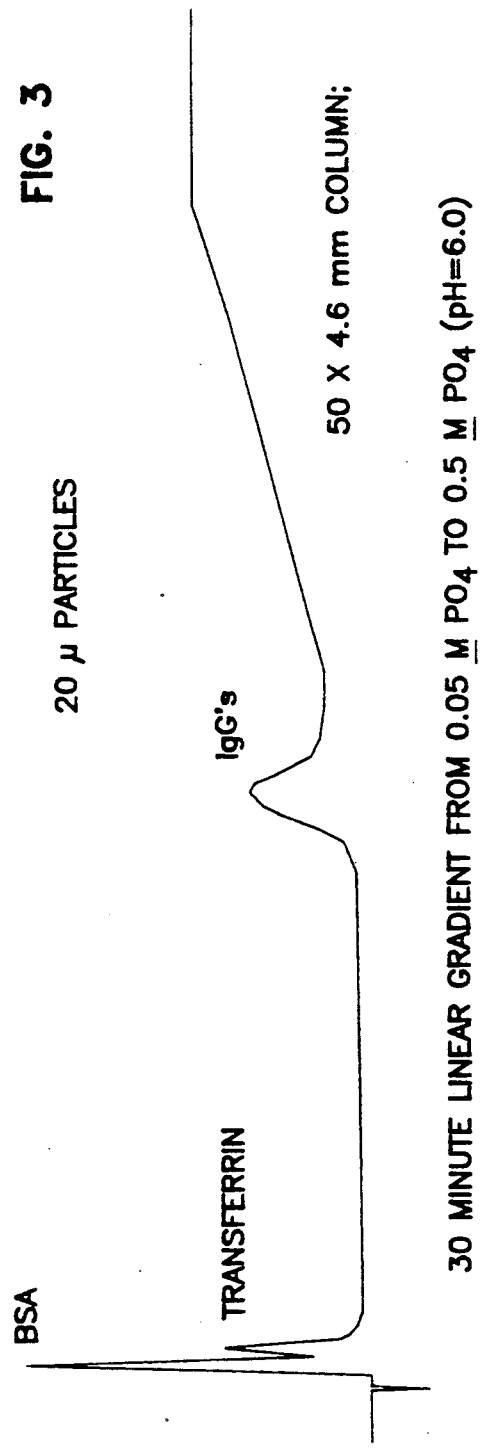

HIGH STABILITY POROUS ZIRCONIUM OXIDE SPHERULES

CROSS-REFERENCE TO RELATED APPLICATION

This is a division of U.S. patent application Ser. No. 07/420,150, filed Oct. 11, 1989, now issued as U.S. Pat. No. 5,015,373, which is a continuation-in-part of U.S. patent application Ser. No. 07/151,819, filed Feb. 3, 1988, now abandoned.

BACKGROUND OF THE INVENTION

A. Inorganic Oxide-Based Chromatographic Supports

Currently known inorganic chromatography supports comprising particulate silica ($SiO_2$) or alumina ($Al_2O_3$) are stable over pH ranges of about 1–8 and 3–12, respectively. The solubilization of $SiO_2$ and $Al_2O_3$ at pHs outside of these ranges results in deterioration of these supports and contamination of the resultant chromatographed and separated products with silicon- or aluminum-containing species. Methods of improving the alkaline stability of particulate $SiO_2$ by cladding the surface with a more base stable metal oxide such as zirconium oxide ($ZrO_2$) have been disclosed in U.S. Pat. Nos. 4,648,975 and 4,600,646. This cladding is disclosed to increase the upper pH limit at which these supports, also referred to as packings, can be used to 11 and 9.5, respectively. However, these packings still lack adequate stability to allow them to be sterilized and cleaned in, for example, 0.1N aqueous sodium hydroxide (NaOH, pH=13).

Use of porous spherical $ZrO_2$ particles on a thin layer chromatography plate has been disclosed in U.S. Pat. No. 4,138,336, a process for the preparation of porous $ZrO_2$ microspheres is taught in U.S. Pat. No. 4,010,242, and chromatographic use of these particles is taught in U.S. Pat. No. 3,782,075. The microspheres are prepared by a process in which colloidal metal oxide particles are mixed with a polymerizable organic material and coacervated into spherical particles by initiating polymerization of the organic material. This is a time consuming, batch process which requires the addition of organic material which is pyrolized and hence lost.

U.S. Pat. No. 3,862,908 discloses microspheres of urania and other metal oxides; however, these particles are fired to near full density, have reduced surface areas and therefore, would not be attractive for chromatographic uses.

U.S. Pat. No. 3,892,580 discloses a process for preparing porous bodies of $ZrO_2$. This process requires the use of a binder to react with the oxide particles during preparation. This binder is subsequently decomposed by pyrolysis and therefore lost. The bodies produced by this process are not spherical, would pack unevenly, may cause increased column pressure, and are therefore not attractive for chromatographic uses.

U.S. Pat. No. 4,389,385 teaches the preparation of porous gels and ceramic materials by dispersing solid particles of an inorganic substance produced by a vapor phase condensation method in a liquid to form a sol. The sol contains colloidal particles which are aggregates of the primary particles. The sol is dried to produce a porous gel of greater than 70% by volume porosity.

B. Reverse Phase High Pressure Liquid Chromatography

The majority of separations employing high pressure liquid chromatography (HPLC) are performed in the so-called reversed-phase mode. In this mode, the column-packing material is referred to as stationary phase. The most commonly used stationary phases feature a non-polar ligand (e.g., octane or octadecane) covalently-bound to a porous silica particle through a siloxane bond (Si—O—Si) to render the surface hydrophobic. Although these silica-based bonded phases are very useful for a wide range of applications in reversed-phase HPLC, their use is strictly limited to the pH range of between 2 and 8, due to the hydrolytic instability of both the silica support particle and the siloxane bond used to "anchor" the non-polar active group. Thus, the production of a pH-stable reversed-phase support material must involve the development of both a stable, controlled porosity, high surface area support material and a method for rendering the surface permanently hydrophobic.

The eluent, also referred to as the mobile phase, used to elute the various components from the stationary phase is relatively polar, e.g., an aqueous buffer or a mixture of water and an organic solvent, e.g., aqueous alcohol. Its polarity can be changed by increasing the concentration of the less polar liquid in the mobile phase, a technique known in the art.

Thus relative to the use of $ZrO_2$-clad silica, a more promising approach to developing a highly stable reversed-phase support, involves replacing the silica with an alternative inorganic material, such as alumina. Although it has been demonstrated that some improvement in pH stability is realized by replacing silica with alumina, the dissolution of alumina in aqueous solutions at extreme pHs (pH<2 and pH>12), even at room temperature, is well known.

As mentioned previously, in addition to the use of a pH-stable support material, the production of a stable, reversed-phase also requires a process for modifying the support material which results in a stable, hydrophobic surface. Silylation is the most widely used method to derivatize silica particles to produce hydrophobic reversed-phase supports. The silylation of inorganic bodies other than silica (e.g., alumina, titania, zirconia, etc.) has been disclosed in U.S. Pat. No. 3,956,179. However, it is uncertain whether or not covalent bonds to the support surface are actually formed. In any event, the hydrolytic instability of the siloxane bond is well known, and it is very likely that a Si-O-metal bond will be even more susceptible to aqueous hydrolysis because of the increased polarity of the bond.

An alternate approach to silylation for modifying the surface polarity of inorganic bodies is the sorption of a polymer of desired polarity/functionality onto an $SiO_2$ or $Al_2O_3$ support surface followed by cross-linking of the individual polymer chains to one another to impart additional stability to the coating. Reversed-phase supports prepared in this fashion exhibit much improved pH stability compared to those prepared by silylation. It is important to recognize that the formation of a stable, cross-linked polymer layer on the surface of the support does not reduce the need for a stable, inorganic support, since it may not be possible to cover the entire inorganic surface. Although cross-linking of the polymer may keep it in place even as the underlying inorganic support dissolves, dissolution of the support will undoubtedly lead to a reduction in the mechanical stability of the support. In addition, problems related to increasing column back pressure are known to accompany the dissolution of the inorganic support and its subsequent appearance in the mobile phase and transport through the column and the accompanying instrumentation.

Another problem related to the use of silica-based reversed phase supports is the difficulty encountered in the chromatography of amines and other basic solutes. This problem results from the presence of acidic silanol groups (SiOH) on the silica surface. Basic solutes undergo very strong interactions with these silanol groups which may involve cation exchange or hydrogen bonding, depending on the pH of the mobile phase. This problem is exaggerated by the requirement of working in the pH range $2<pH<8$ on silica-based columns, since most amines will be protonated in this pH range and protonated amines can readily bond to the silica surface. One obvious approach to improving the chromatography of amines is to work at hydrogen ion concentrations significantly lower than the ionization constant of the amines so that they are unprotonated. For aliphatic amines, this normally involves working at a pH greater than 11. However, these pH ranges cannot be employed using silica-based columns.

The presence of the aforementioned acidic silanol groups can also lead to irreversible adsorption of many classes of organic molecules onto silica-based reversed-phase supports, a problem which is well known to those versed in the art. This irreversible adsorption is particularly troublesome in the reversed-phase HPLC of proteins. Ultimately, this adsorption will result in a change in the properties of the support and can lead to its destruction.

Reversed-phase HPLC is finding increased use in the area of bioprocessing because of HPLC's great ability to separate and purify materials. At the preparative scale, there are many unique considerations not applicable at the analytical scale. One such consideration is the need to sterilize a chromatography column prior to its use in the purification of a product intended for biological or human use. Another is the desirability of using larger particles, typically greater than $20\mu$ in average particle diameter.

C. Ion-Exchange High Pressure Liquid Chromatography

Ion-exchange chromatography (IEC) has become an important separation technique for the purification of biomolecules. Typical supports used in IEC are silica, alumina, agarose, polymethacrylate, and poly(styrenedivinylbenzene). See H. G. Barth et al., *Anal. Chem.*, 60, 387R (1988). Agarose is not suitable for high pressure work, while silica and alumina have limited pH stability. The matrices of silica and alumina must also be derivatized or coated to provide the support with ion exchange properties. This often introduces hydrophobic interactions into the retention mechanism. The hydrophobic nature of hydrocarbon-based supports such as poly(styrene-divinylbenzene) must be masked in order for them to be used as IEC supports. The hydrocarbon-based supports are also subject to shrinking and swelling whereas inorganic supports are not.

Zirconium phosphate has been extensively studied as an inorganic ion exchanger for the nuclear industry because of its excellent exchange capacities, radiation and thermal stability. See A. Clearfield et al., *Ion Exchange and Solvent Extraction*, J. A. Marinsky et al., eds., Marcel Decker, New York, (1973) at Chapter 1. However, relatively little work has been done using zirconium phosphate as an HPLC support because of its poor mechanical properties and the lack of materials with the necessary porous structure. Furthermore, zirconium phosphate lacks the mechanical stability necessary for high performance chromatographic supports.

OBJECTS OF THE INVENTION

It is, therefore, an object of the present invention to produce chromatography column support material which resists dissolution and is therefore stable in aqueous media over a wide pH range.

Furthermore, it is an object of the present invention to produce a reverse phase support material which possesses a hydrophobic surface and can therefore be used for reverse phase chromatographic processes, and which may be exposed to solutions having pHs of from about 1 to 14 without undergoing significant dissolution.

Furthermore, it is an object of the present invention to produce a support material comprising a non-polar surface which can be used for separation by both ion-exchange and reversed-phase processes, wherein the relative contribution of these two processes may be controlled by simple adjustment of mobile phase conditions.

Also, it is the object of the present invention to produce a support material which can be regenerated by freeing it from "irreversibly adsorbed" biological or organic residues by treatment at high pH.

It is another object of the present invention to provide a support material for use in large scale separations, particularly of products generated by biotechnology, for example, by fermentation, wherein said support material can withstand traditional sterilization techniques involving high pH and heat treatment.

SUMMARY OF THE INVENTION

The present invention provides a support material adapted for use as the stationary phase in high-performance liquid chromatography (HPLC) which comprises porous spherules of zirconium oxide ($ZrO_2$, "zirconia"). These spherules display a remarkable physical and chemical stability in aqueous media of a pH of about 1 to 14. Preferred $ZrO_2$ spherules are about $0.5-500\mu$, most preferably about $20-500\mu$ in diameter, have a surface area of about $1-200$ m$^2$/g, most preferably about $40-150$ m$^2$/g; and have pore diameters of from about $20-500$ Å, most preferably about $100-300$ Å.

The $ZrO_2$ spherules of the invention can be prepared by a process consisting essentially of (a) dispersing an aqueous sol containing colloidal $ZrO_2$ particles in a medium which extracts the water from the dispersed sol to afford gelled $ZrO_2$ spherules; (b) recovering the gelled spherules from the medium; and (c) heating the gelled spherules to yield solid porous $ZrO_2$ spherules. This process yields porous particles of $ZrO_2$ which are essentially spherical. When formed into a bed, the spherules provide improved mobile phase flow characteristics over those exhibited by irregularly-shaped, jagged-edged or angular particles.

In a preferred embodiment of this process, the colloidal $ZrO_2$ sol is centrifuged, the supernatant liquid decanted and the residue re-dispersed in an about equal volume of water. This procedure is preferably repeated a plurality of times ($2-5\times$). The re-dispersed $ZrO_2$ yields spherules having a larger pore diameter and an increased pore volume, when they are formed in accord with the present method.

These particulate spherules can be formed into a bed, and employed as the stationary phase in separations performed via chromatography. Therefore, the spherules can be used as the stationary phase in conventional chromatography columns which have an axial flow path, with or without rigid walls. For example, the $ZrO_2$ spherules can be packed into a column such as a HPLC column, where the packing functions as the stationary phase during HPLC separations which are accomplished by ion exchange and size exclusion processes. The spherules can also be used in columns which have a radial flow path or to form a fluidized bed, with single or multiple stage absorbers. The bed can also be formed of a mass of spherules which are contained in an immobilized enzyme reactor or other type of bioreactor.

The majority of HPLC methodologies involve use of the reverse phase mode, wherein the column-packing material (stationary phase) is non-polar, and the mobile phase is polar. Therefore, the present invention also provides a support material comprising porous $ZrO_2$ spherules coated with a hydrophobic polymeric layer. The coated spherules are prepared by adsorbing a polymerizable monomer or oligomer onto the surface of the spherules and subsequently cross-linking it, e.g., by reaction of the adsorbed material with a free radical initiator or by irradiation. The polymeric coating renders the $ZrO_2$ particles hydrophobic without substantially altering any of their desirable physical and mechanical properties. Likewise, the $ZrO_2$ spherules can be coated with a hydrophilic, cross-linked polymer to form an ion-exchange support material.

The coated spherules can also be combined with a suitable binder and used to coat a glass or plastic substrate to form plates for thin-layer chromatography.

Therefore, another preferred embodiment of the present invention is directed to a chromatographic support material comprising porous $ZrO_2$ spherules having a cross-linked polymeric coating thereon, wherein said coated spherules are hydrophobic, have a pore size from about 20–500 Å and an average diameter of about 0.5–500μ.

As a result of the support material's remarkable stability over a wide pH range, it is useful for the chromatographic separation of compounds at their optimal pHs. For example, the coated material prepared in this fashion can be used for the separation of amines at a variety of pHs and mobile phase conditions such that the separation occurs either by a reversed-phase retention mode, a cation-exchange mode, or some combination of the two. For example, at high pH (pH=12), the amines are unprotonated so that separation occurs entirely by a reversed-phase mode. At low pH in the presence of a low ionic strength phosphate buffer and with an organic solvent-rich mobile phase, the separation occurs via a cation-exchange mode. By adjustment of mobile-phase conditions, selectivity can thus be significantly adjusted.

The $ZrO_2$ spherules of the present invention can also be employed to immobilize bioactive materials for a variety of purposes, including catalysis, analysis, affinity chromatography and synthetic transformations. Bioactive materials can be strongly sorbed onto the exterior and interior surfaces of both the uncoated and the polymer-coated $ZrO_2$ spherules, while retaining a large percentage of their initial bioactivity. Useful biomaterials include proteins such as enzymes and antibodies.

In addition, "irreversibly adsorbed" organic or biological residues can be removed from fouled columns packed with coated or uncoated spherules by flushing the column with a mobile phase at high pH or by injecting pulses of the high pH mobile phase. The term "irreversible adsorption" refers to the very strong tendency which surface-adsorbed proteins, biopolymers and the like exhibit to remain sorbed under normal elution conditions, until the mobile phase conditions are changed sufficiently to desorb them.

Therefore, coated or uncoated $ZrO_2$ spherules can be prepared which comprise a biologically active material such as an enzyme or a protein such as an immunoglobulin. Upon depletion of the biological activity, the enzyme or other protein can be removed from the spherules by exposing them to an aqueous medium at high pH, e.g., by washing them with a solution of an alkali metal hydroxide. The spherules, stripped of the biological materials, can then be treated with a buffer to return them to a physiological pH, and subsequently reloaded with the same, or a different bioactive material.

The $ZrO_2$ spherules may also be exposed in situ to traditional sterilization conditions, for example, by exposing the packing or the packed column to heat and high pH, without significant degradation.

In a further preferred embodiment of the invention, the surface of the coated or uncoated $ZrO_2$ spherules is deactivated or modified by treatment with an effective amount of an inorganic phosphate, such as phosphoric acid or an alkali metal phosphate salt, or with an organophosphonate, prior to or following application of the hydrophobic polymer coating. The treatment conditions can be varied so as to either reversibly adsorb phosphate, which may be phosphate ion, onto the $ZrO_2$ surface, or to bind the phosphate onto and/or into the $ZrO_2$ surface, for example, as zirconium phosphate. These treatments render the particles effective to separate negatively charged molecules such as sulfonates, carboxylates, and other oxyanions. It is also believed that the organophosphonate becomes incorporated into the organic matrix of the polymeric coating.

BRIEF DESCRIPTION OF THE DRAWINGS

FIG. 1 is a schematic depiction of a chromatographic separation of a protein mixture, utilizing an HPLC column packed with inorganic phosphate-treated $ZrO_2$ spherules prepared according to the present invention.

FIG. 3 is a schematic depiction of a chromatographic separation of a mixture of IgG monoclonal antibodies, albumin and transferrin, utilizing an HPLC column packed with inorganic phosphate-treated $ZrO_2$ spherules prepared according to the present invention.

DETAILED DESCRIPTION OF THE INVENTION

I. Zirconium Oxide

Figure 2:
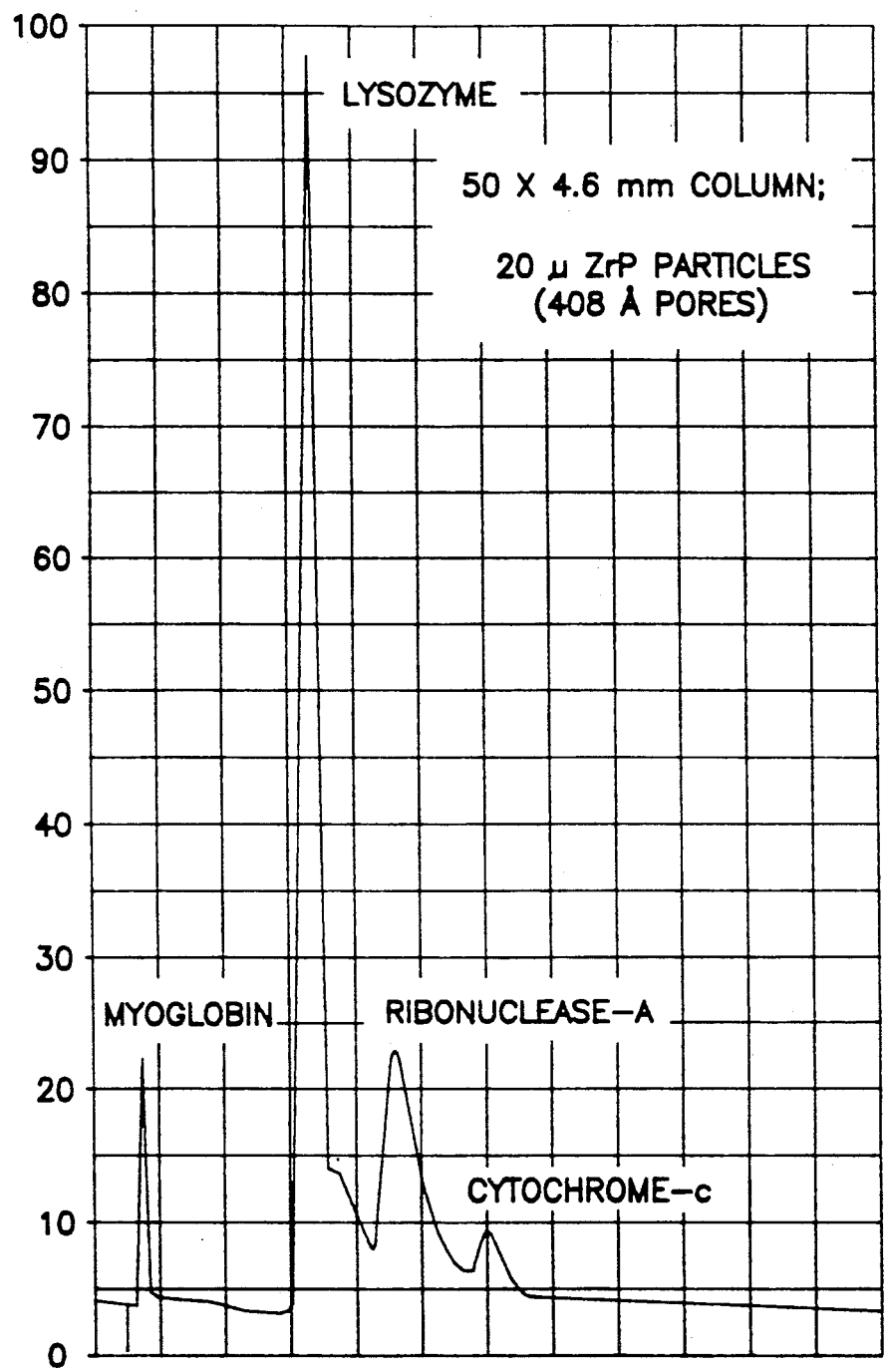
FIG. 2 is a schematic depiction of a chromatographic separation of a protein mixture, utilizing an HPLC column packed with inorganic phosphate-treated $ZrO_2$ spherules prepared according to the present invention, and a mobile phase to which 1.0 mM potassium phosphate was added.

In the practice of this invention, a portion, or preferably a majority of the initial zirconium oxide ($ZrO_2$) used to form the present spherules is in the sol state; a colloidal dispersion of $ZrO_2$ particles in water.

Colloidal dispersions of zirconium oxide suitable for use as the $ZrO_2$ source used to prepare the present spherules are manufactured by Nyacol Inc., Ashland, Mass. These dispersions contain about 20 wt-% $ZrO_2$, wherein the $ZrO_2$ particles vary in average diameter, e.g., from about 10-250 nm. For example, Nyacol ™ Zr 95/20 is an aqueous dispersion containing 20 wt-% $ZrO_2$ of colloidal $ZrO_2$ particles, the majority of which are about 95 nm in diameter.

Non-colloidal $ZrO_2$ sources may be included along with the colloidal $ZrO_2$ particles used to prepare these spherules. Thus, chloride, nitrate, sulphate, acetate, formate or other inorganic or organic salts of zirconium such as the oxysalts and alkoxides may be included with the $ZrO_2$ sol and the mixture used to make spherules. In preferred mixtures, colloidal $ZrO_2$ particles make up a major part of the total $ZrO_2$ present.

Organic compounds may also be included with the $ZrO_2$ precursors used to prepare the spherules. These organic materials are fugitives which are removed during the firing of the spherules. In particular, water-soluble polymers such as polyvinylpyrrolidone, polyethylene glycol, polyethylene oxide, and the like, or latex particles may be included in the liquid mixture used to prepare the spherules. These fugitives may be added to alter the rheology of the precursor solution or the pore structure of the resulting fired spherule.

It is also within the scope of the present invention to include precursors for other metal oxides with the $ZrO_2$ precursors so as to stabilize a particular crystalline phase of $ZrO_2$ or to retard grain growth in the fired spherules. Thus, salts or sols of metals such as yttrium, magnesium, calcium, cerium, aluminum, and the like may be included in levels of from approximately 0-20 mole-%. $ZrO_2$ spherules fired in air or in oxidizing atmospheres which do not contain other oxide additives display either monoclinic, tetragonal or pseudocubic crystal structures when cooled to room temperature. Higher firing temperatures and longer firing times favor the presence of the monoclinic phase. The inclusion of other metal oxides allows the preparation of spherules which possess either monoclinic, tetragonal, or cubic crystalline structures.

II. Preparation of $ZrO_2$ Spherules

To prepare the spherical $ZrO_2$ particles, or "spherules" of the present invention, an aqueous sol containing a colloidal dispersion of $ZrO_2$ particles is dispersed in a medium which can extract water from the dispersed sol in the form of droplets. Removal of all or a portion of the water results in gelled solid spherules which consist of aggregated sol particles. One medium which may be used is 2-ethyl-1-hexanol as disclosed in U.S. Pat. No. 4,138,336. A preferred medium for safety reasons and ease of processing is peanut oil, which is preferably used at a temperature of about 80°-100° C. The most preferred medium is a mixture of peanut oil and oleyl alcohol which are combined in a ratio of about 1:1, and used at a temperature of about 80°-100° C. Oleyl alcohol possesses a higher extraction capacity than peanut oil and mixtures of the two allow the extraction capacity of the medium to be controlled. Depending upon the ratio of sol to forming medium extraction times of from about 1-60 minutes can be used to fully gel the $ZrO_2$ particles. The gelled spherules may be conveniently separated from the extracting medium, e.g., by filtration.

The spherules of the present invention may also be prepared by spray drying a suitable zirconium precursor, as disclosed in U.S. Pat. No. 4,138,336. It is difficult to prepare spherical particles larger than about 45µ in diameter when using the spray drying process, however.

Once the $ZrO_2$ particles are condensed into spherules by one of the above processes, thermal treatment at firing temperatures of from about 100°-1500° C., preferably about 400°-1100° C., is performed. The resulting fired spherules may be from about 0.5-500µ in diameter and can possess a surface area of 1-200 $m^2/g$ and pore diameters of from about 20-500 Å. These particles have high mechanical strength and exceptional stability to aqueous solutions of pHs of about 1-14.

The particles may be packed into a HPLC column and used to perform HPLC chromatographic separations by ion exchange and size exclusion mechanisms. For a general discussion of HPLC techniques and apparatuses, see *Remington's Pharmaceutical Sciences*, A. Osol, ed., Mack Publishing Col, Easton, Pa. (16th ed. 1980), at pages 575-576, the disclosure of which is incorporated by reference herein.

III. Polymer-Coated $ZrO_2$ Spherules

The majority of HPLC methodology employs the so-called "reverse phase" mode, i.e., the column-packing material (stationary phase) is non-polar and the eluent (mobile phase) is polar. Therefore, it is preferred to coat the surface of the $ZrO_2$ spherules with a hydrophobic coating, which is also preferably stable to aqueous solutions having a pH of about 1-14. Hydrophilic polymer coatings can also be applied and cross-linked for modification of the $ZrO_2$ spherules to form an ion exchange support or a steric exclusion support. These hydrophilic polymer coatings are formed from monomers or oligomers which comprise polar groups such as sulfonic acids, carboxylic acids, amino groups, hydroxyl groups, amido groups or quaternary ammonium groups. A preferred method to prepare such a coating comprises sorbing a polymerizable monomer or oligomer onto the surface of the spherules, and cross-linking the monomer or oligomer. See G. Shomberg, *LC-GC*, 6, 36 (1988).

A. Polymerizable Monomers or Oligomers

A wide variety of cross-linkable organic materials, which may be monomers, oligomers or polymers, can be employed to coat the porous $ZrO_2$ spherules. For example, such materials include polybutadiene, polystyrene, polyacrylates, polyvinylpyrrolidone (PVP), polyvinyl alcohol (PVA), polyorganosiloxanes, polyethylene, poly(t-butyl)styrene, polyisoprene, polyethyleneimine, polyaspartic acid and multifunctional silanes.

A preferred material for the preparation of a reversed phase support material is an oligomer of polybutadiene. A preferred material for modification of the $ZrO_2$ spherules to form a cation ion exchange support is polyaspartic acid. A preferred material for construction of a support suitable for aqueous steric exclusion chromatography is a tri- or di-alkoxy-,gamma-glycidoxy silane.

B. Cross-linking Agents

Any of the common free radical sources including organic peroxides such as dicumyl peroxide, benzoyl peroxide or diazo compounds such as 2,2'-azobisisobutyronitrile (AIBN) may be employed as cross-linking agents in the practice of the present invention. Useful commercially available peroxyesters include the alkylesters of peroxycarboxylic acids, the alkylesters of monoperoxydicarboxylic acids, the dialkylesters of diperoxydicarboxylic acids, the alkylesters of monoperoxycarbonic acids and the alkylene diesters of peroxycarboxylic acids. These peroxyesters include t-butyl peroctoate, t-butyl perbenzoate, t-butyl peroxyneodecanoate and t-butyl peroxymaleic acid. These compounds are commercially available from Pennwalt Chemicals, Buffalo, N.Y. The amount of any free radical initiator required to catalyze the polymerization reaction will vary depending upon the molecular weight of the initiator and its thermal stability. Oligomers may also be polymerized by thermal treatment, by irradiation with UV light or gamma rays or by exposure to high energy electrons.

C. Coating/Cross-linking Process

Zirconium oxide may be modified in different ways to achieve materials with a light, intermediate or heavy carbon load. Preferably, the $ZrO_2$ spherules are first surface-hydrated and then dried in vacuo. Depending on the load desired, the dried $ZrO_2$ spherules are added to 15-50 ml of a pentane solution containing from 5-250 mg of an oligomer, such as polybutadiene, per gram of $ZrO_2$ spherules. The resultant slurry is placed in an ultrasonic bath and a vacuum applied in order to degas the particles and to insure that the oligomer solution has infiltrated substantially all of the pores. A free radical initiator, such as dicumyl peroxide, is then added at a level of 2-20% (w/w) relative to the amount of polymer used. Solvent is then removed either by evaporation or by filtration, again depending on the desired carbon load. The treated $ZrO_2$ spherules are then heated to about 60°-70° C. under vacuum (10-20 mm Hg) for 12 hrs to remove any remaining solvent. The cross-linking reaction is then carried out by heating the coated $ZrO_2$ spherules in a tube furnace at 175°-200° C. for 2-4 hours under a flow of nitrogen.

The resultant coated spherules can then be packed into 5 cm×0.46 cm HPLC columns by dry packing or stirred upward slurry packing, depending on their particle size.

Mixed-mode chromatography of amines can be performed in aqueous/organic mobile phases at various pHs containing different amounts of organic solvent, phosphate buffer and neutral salt for ionic strength adjustment.

A column "fouled" by repeated injections of large amounts of material, to the point that a marked change in characteristics is observed, can be stripped of irreversibly adsorbed material. The original column performance can be restored by pulsing the column with 100 μl injection of 1M NaOH or by flushing the column for about 0.5-10 hrs with aqueous alkali metal hydroxide, i.e., with a 0.1M NaOH solution.

The stability of the polymer-coated $ZrO_2$ spherules or uncoated $ZrO_2$ spherules to sterilizing conditions can be demonstrated by heating a previously characterized column to 100° C. while pumping a 1M NaOH solution through it for 1-4 hrs. Recharacterization of the column demonstrates that no significant change in column properties or decreased retention of a non-polar substance has taken place.

IV. Bioactive Materials

A wide variety of bioactive materials can be bound to the uncoated or polymer-coated spherules by presently-available techniques so that their bioactivity is retained and prolonged, or "stabilized" with respect to the unbound bioactive material. For example, antibodies or enzymes can be bound to the uncoated spherules in high concentrations by agitating an aqueous mixture of degassed spherules and antibody in a buffer, e.g., for about 0.1-5 hrs under ambient conditions. For a review of other noncovalent and covalent enzyme-binding methodologies, see R. A. Messing (U.S. Pat. No. 3,850,751), the disclosure of which is incorporated by reference herein.

Enzymes capable of being bound and stabilized as described herein include a wide variety of enzymes which may be classified under six general groups: hydrolytic enzymes, redox enzymes, transferase enzymes, lyases, isomerases and ligases. The first group, hydrolase enzymes include proteolytic enzymes which hydrolyze proteins, e.g., papain, ficin, pepsin, trypsin, chymotrypsin, bromelin, keratinase, carbohydrases which hydrolyze carbohydrates, e.g., cellulase, glucuronidase, amylase, maltase, pectinase, chitinase; esterases which hydrolyze esters; e.g., lipase, cholinesterase, lecithinase, phosphatase; nucleases which hydrolyze nucleic acid, e.g., ribonuclease, deoxyribonuclease; and amidases which hydrolyze amines, e.g., arginase, asparaginase, glutaminase, and urease. The second group are redox enzymes that catalyze oxidation or reduction reactions. These include glucose oxidase, catalase, peroxidase, lipoxidase, and cytochromes. The third group are transferase enzymes that transfer groups from one molecule to another. Examples of these are glutamic-pyruvic transaminase, glutamic-oxalacetic transminase, transmethylase, phosphopyruvic transphosphorylase and dehydrogenase. The fourth group are lyase enzymes that catalyze the cleavage of C-C, C-O, C-N and other bonds by elimination, leaving double bonds, or conversely, adding groups to double bonds. Examples of these are pyruvate decarboxylase, amino acid decarboxylases, aldolase, fumarate hydratases, aconitate hydratases and ammonia lyase. The fifth group are isomerase enzymes that catalyze the dehydrogenation and epimerization of amino acids and sugars. An example of an isomerase is phosphoglucomutase. The sixth group are ligase enzymes that catalyze the synthetic linking of two molecules, simultaneously with the breakdown of ATP. Examples of these are aminoacyl-tRNA synthetases and biotinyl-dependent carboxylases.

Other proteins capable of being bound and stabilized as described herein include Con-A, Protein-A, acid glycoproteins, plasma immunoglobulins, monoclonal antibodies, bioactive polypeptides such as serum proteins and immunomodulators, e.g., lymphokines and the like. Other examples of proteins which are bound by the present spherules are provided in the working example hereinbelow.

V. Phosphate Modification

The surface of uncoated or polymer-coated $ZrO_2$ spherules can be easily and dramatically modified in a chromatographically-beneficial way by treatment with aqueous inorganic phosphate solutions. The combination of polymer coating and phosphate treatment produces a mixed mode stationary phase exhibiting both cation-exchange and reversed-phase properties. This allows one to adjust the selectivity of the present support material with respect to a group of basic solutes by appropriate adjustment of mobile phase pH, ionic strength, and reversed-phase eluting strength (i.e., volume fraction of the adjuvant organic solvent).

Useful aqueous inorganic phosphate solutions include about 0.01-1.0M solutions of phosphoric acid ($H_3PO_4$) or of alkali metal phosphate salts, e.g., orthophosphates, pyrophosphates, metaphosphates, tripolyphosphates and the like.

Although phosphate ions can be adsorbed onto the $ZrO_2$ surface by exposure to dilute (0.01-0.05M) aqueous solutions of various inorganic phosphates for relatively short periods of time (e.g., 1-3 hours) at ambient temperatures (20°-30° C.), the phosphate is slowly removed from the surface under conditions of high pH. Therefore, it is preferred to treat the surface of the $ZrO_2$ spherules with relatively concentrated (0.05-1.0M) aqueous solutions of inorganic phosphates for longer periods of time (three or more hours) and/or at elevated temperatures (e.g., 90°-110° C.), so that the phosphate ions react with and become incorporated into an outer layer of the spherule, for example, as, e.g., zirconium phosphate. Preferably, the treated spherules will comprise about 0.5-15.0 wt-% phosphate.

This phosphate incorporated into the structure as zirconium phosphate is less readily removed by hydrolysis reactions than the surface adsorbed phosphate ions are by exchange processes. Both of these types of phosphate groups will nevertheless be gradually lost upon exposure to conditions of high pH (>10) in flowing mobile phases. This loss of phosphate can be reduced by keeping phosphate present in the mobile phase. Additionally, it is also possible to recondition a column which has lost phosphate by exposing it to phosphating conditions.

It is important to note that the underlying $ZrO_2$ spherules remain stable. It is therefore possible to perform an ion exchange separation with a column packed with phosphate-coated spherules, clean the column by flushing with strong base, and if necessary expose the column to phosphating conditions prior to the next separation operation. These cycles may be repeated indefinitely.

For purposes of calculating wt-% phosphate in the treated spherules, it will be assumed that each phosphate ion incorporated into the $ZrO_2$ spherule possesses four oxygen atoms. The weight percentage of phosphate can thus be calculated from a knowledge of the weight percentage of phosphorus in the spherule by the following formula:

$$\text{wt-\% phosphate} = \text{wt-\% phosphorus} \times \frac{95 \text{ [molecular wt. } PO_4]}{31 \text{ [atomic wt. P]}}$$

The weight percentage of phosphorus in the spherules can be measured by inductively coupled plasma spectroscopy (ICP). The amount of phosphorous incorporated in the spherules for a given exposure condition is directly related to the specific surface area of the $ZrO_2$ spherule.

For example, treatment of the $ZrO_2$ spherules having a specific surface area of about 117 $m^2/g$ for about 1-4 hours at about 25° C. with an excess of an aqueous solution of phosphoric acid with a concentration from about 0.01-1.0 molal yields particles containing about 2.0-5.0 wt-% phosphate. Treatment of $ZrO_2$ spherules for about 1-4 hours at about 100° C. with an excess of about 0.01-1.0 molal $H_3PO_4$ yields spherules containing about 2.0-12.0 wt-% phosphate.

Although not intending to be bound by any particular theory of action, it is believed that these more rigorous treatment conditions, including temperatures of about 90°-110° C., cause the phosphate ions to chemically react with and be incorporated into the $ZrO_2$ spherules. Thus, the outer surfaces (both external and internal) of the spherules are at least partially converted to zirconium phosphate. The thickness of this zirconium phosphate layer is governed by the reaction conditions employed. Higher phosphate concentrations, higher temperatures and longer reaction times lead to the formation of thicker layers. These particles exhibit desirable cation exchange properties, while retaining the high mechanical and pH stability exhibited by untreated particles. As discussed above, while less stable at elevated pHs and temperatures than the underlying $ZrO_2$ particles, the phosphate coatings possess useful stabilities and can be readily regenerated by exposure to solution sources of inorganic phosphate.

VI. Modification with Organophosphorus Compounds

For some applications, it is desirable to further deactivate or modify the surface of the uncoated or polymer-coated $ZrO_2$ spherules. This can be accomplished by treating the uncoated $ZrO_2$ spherules with an organophosphorus compound in a suitable solvent for the organophosphorus compound. Preferred organophosphorus compounds include the saturated or unsaturated organophosphonic acids and the water-soluble salts thereof, e.g. the alkali metal salts. Useful organophosphorus compounds include organophosphonates such as allylphosphonates, octyl phosphonates, diallyl phosphorates, allylphosphonic acid, phenyl phosphonic acid, naphthyl phosphonic acid, phenyl phosphinic acid, phenylphosphoric acid, and the salts thereof.

Useful solvents for the organophosphorus compound include aqueous alcohol, e.g., a solution of water and a ($C_1$-$C_5$) alkanol. The $ZrO_2$ spherules are preferably coated by agitating the spherules in a solution of the organophosphorus compound so that the weight ratio of the organophosphorus compound to spherules is about 0.25-1:1. The treated particles are then separated from the treating solution, and dried. The cross-linked polymeric coating then can be applied as disclosed hereinabove.

The invention will be further described by reference to the following detailed examples.

EXAMPLE 1

Preparation of ZrO$_2$ Spherules

Peanut oil (3 liters) was placed in a 4 liter beaker and heated to 90° C. A mechanical agitator was inserted and the peanut oil was vigorously stirred. One hundred grams of Nyacol TM Zr 95/20, a colloidal ZrO$_2$ manufactured by Nyacol, Inc. and containing 20 wt-% of ZrO$_2$, primarily as about 95 nm particles, was sprayed into the peanut oil through an aerosol atomizer. After approximately 30 minutes, the batch was filtered through a No. 54 Whatman filter. Approximately 17 g of solids were recovered, which are predominately spherules having a diameter of <30μ.

EXAMPLE 2

Preparation of ZrO$_2$ Spherules

Peanut oil (600 g) and 600 g of oleyl alcohol were mixed and heated to about 90° C. Under vigorous agitation, 100 g of Nyacol TM Zr 95/20 was sprayed into the peanut oil/oleyl alcohol mixture as described in Example 1. After 30 minutes, the batch was filtered and the particles collected. The particles were predominately (ca. 70%) spherules having a diameter of <50μ.

Spherules prepared as described in Examples 1 and 2 were thermally treated at a series of temperatures and the surface area, average pore diameter and pore volume were measured by nitrogen adsorption isotherm on a Quantasorb surface area analyzer. These results are summarized in Table I, below.

TABLE I

| Firing Temp (°C.)* | Surface Area (m$^2$/g) | Average Pore Diameter (Å) | Pore Volume (%) |
| --- | --- | --- | --- |
| 400 | 142 | 42 | 47 |
| 500 | 92 | 71 | 50 |
| 600 | 34 | 110 | 36 |
| 800 | 17 | 205 | 34 |
| 900 | 14 | 220 | 31 |

*6 hrs

The data summarized on Table I show that it is possible to increase the average pore diameter by increasing the firing temperature from 400° to 900° C. The surface area and pore volume decrease with increasing firing temperature. Chromatographic activity of the ZrO$_2$ spherules is determined by the parameters of the surface area, average pore diameter and pore volume. Accordingly, the appropriate firing temperature is selected.

EXAMPLE 3

Preparation of ZrO$_2$ Spherules

The procedure of Example 2 was used to prepare spherules using Nyacol TM Zr 50/20 (50 nm ZrO$_2$ colloidal size) as the ZrO$_2$ source.

EXAMPLE 4

Preparation of ZrO$_2$ Spherules

The procedure of Example 2 was used to prepare spherules using Nyacol TM Zr 150/20 (150 nm ZrO$_2$ colloid size) as the ZrO$_2$ source.

Table II summarizes the surface area, average pore diameter and pore volume of spherules prepared as per Examples 2-4 and fired at 600° C. for 6 hrs.

TABLE II

| ZrO$_2$ Source* | ZrO$_2$ Colloid Size (nm) | Surface Area (m$^2$/g) | Average Pore Diameter (Å) | Pore Volume (%) |
| --- | --- | --- | --- | --- |
| Zr 50/20 | 50 | 33 | 92 | 31 |
| Zr 95/20 | 95 | 34 | 110 | 36 |
| Zr 150/20 | 150 | 40 | 147 | 45 |

*Nyacol TM series.

The data summarized in Table II show that it is possible to control the average pore diameter of the fired spherules by appropriate selection of the colloid size of the ZrO$_2$ source. Larger colloids produce fired spherules with larger pore diameters and pore volumes.

EXAMPLE 5

Preparation of ZrO$_2$ Spherules

Preparation A

A 4500 g sample of Nyacol TM Zr 100/20, which contained 20 wt-% ZrO$_2$ primarily as about 100 nm particles, was concentrated on a rotary evaporator until its concentration was 35% ZrO$_2$ by weight. This sol was then spray dried on a spray drier manufactured by Nyro Incorporated. About 900 g of dried solids were obtained. When examined under an optical microscope, the solids were observed to be spherules from about 0.5 to 30μ in diameter. The dried spherules were fired by heating them in a furnace to a temperature of 600° C. over 6 hours, with additional heating applied at a constant temperature of 600° C. for 6 more hours. Nitrogen adsorption measurements on the fired ZrO$_2$ spherules indicated that their average surface area was 48.1 m$^2$/g and their average pore diameter was 116 Å. The spherules were air classified, and the fraction ranging in size from approximately 5-10μ was subsequently used for chromatography experiments.

Preparation B

To prepare spherules with larger diameter pores than those of Preparation A, the procedure described below was followed. 1200 g of Nyacol TM Zr 100/20 colloidal ZrO$_2$ were centrifuged on a laboratory centrifuge at 5000 rpm for 55 minutes. The supernatant was discarded and the sediment was re-dispersed in distilled water. The centrifuged sol was placed on a rotary evaporator and concentrated until it contained 35% by weight of ZrO$_2$. Following spray drying of the sol under conditions similar to those described in Preparation A, about 300 g of dried solids were obtained. When examined under an optical microscope, the solids were observed to be spherules ranging in size from about 1 to 30μ in diameter. Many of the spherules (>50%) were observed to possess cracks, especially those spherules of larger size.

A portion of the fired spherules was then placed in a furnace and heated to a temperature of 1100° C. over 9 hours, with additional heating at a constant temperature of 1100° C. for 6 more hours. The surface area of the fired spherules was determined to be 16.1 m$^2$/g, and the average pore diameter was 408 Å, as measured by mercury porosimetry. This technique is a preferred method for measuring the size of pores greater than about 250 Å in diameter. The fired spherules were unchanged in appearance from the dried spherules. They were nearly all intact, but many (>50%) were cracked.

A portion of the fired spherules was classified by size fraction as described in Preparation A. Examination of the classified fractions indicated that a portion of the spherules had fractured during the classification procedure. Many intact spherules remained, but a portion of each fraction contained irregularly shaped particles which appeared to have been produced by the fracturing of the spherules during the classification process.

Preparation C

To prevent the cracking observed in the spherules prepared according to Preparation B, spherules were also prepared as follows: 1250 g of Nyacol ™ Zr 100/20 colloidal $ZrO_2$ were placed in a laboratory centrifuge and spun at 5000 rpm for 55 minutes. The supernatant was discarded and the sediment was re-dispersed in distilled water. This centrifuged sol was placed on a rotary evaporator and concentrated until the concentration of $ZrO_2$ in the sol was 32 wt %. To 513 g of this sol were added 34.6 g of a solution of zirconyl acetate containing 25% by weight $ZrO_2$ equivalent (Harshaw, Inc., Cleveland, Ohio), and 61 g of a solution containing 50 wt % PVP K30, a polyvinylpyrrolidone polymer (GAF Corporation, Texas City, Tex.) were added to the concentrated sol. The resulting mixture was then agitated rapidly into a 50/50 mixture of peanut oil and oleyl alcohol which had been heated to a temperature of 90° C. The resulting mixture contained gelled spherules of about 1 to 30μ in diameter, which were observed under an optical microscope to be intact and crack-free.

The spherules were then fired to a temperature of 900° C. over 7 hours and 20 minutes, with heating at a constant temperature of 900° C. for an additional 6 hours. After firing, the resulting spherules were from about 1 to 25μ in diameter, and were observed under an optical microscope to be intact and crack-free. The surface area and average pore diameter of these microspheres were measured by mercury porosimetry to be 28 $m^2/g$ and 415 Å, respectively. A portion of these spherules was classified into 5-10μ and 10-20μ fractions by sieving. Following classification, the classified spherules remained uncracked and intact.

EXAMPLE 6

Preparation of $ZrO_2$ Spherules with Single Centrifugation

Nyacol ™ Zr 95/20 colloidal $ZrO_2$ was placed in a laboratory centrifuge and sedimented. The supernatant was decanted and discarded. The sedimented $ZrO_2$ was re-dispersed in an equal volume of distilled water. Spherules were prepared from this centrifuged sol following the procedures of Example 2.

EXAMPLE 7

Preparation of $ZrO_2$ Spherules with Double Centrifugation

The centrifugation procedure of Example 6 was performed and the re-dispersed sol was subsequently recentrifuged to sediment, the supernatant decanted and the $ZrO_2$ re-dispersed. Spherules were prepared from this doubly centrifuged sol following the procedure of Example 2.

EXAMPLE 8

Preparation of $ZrO_2$ Spherules with Triple Centrifugation

The double centrifugation procedure used in Example 7 was performed and the re-dispersed sol was subsequently re-centrifuged to sediment, the supernatant decanted and the $ZrO_2$ re-dispersed. Spherules were prepared from this triply centrifuged sol following the procedures of Example 2.

Table III summarizes the surface area, pore diameter and pore volume of spherules prepared as per Examples 2, 6, 7 and 8, and heated to 600° C. for 6 hrs.

TABLE III

| $ZrO_2$ Source* | Surface Area ($m^2/g$) | Average Pore Diameter (Å) | Pore Volume (%) |
|---|---|---|---|
| Zr 95/20 | 34 | 110 | 36 |
| Zr 95/20 cent. (1x) | 50 | 162 | 55 |
| Zr 95/20 cent. (2x) | 52 | 235 | 62 |
| Zr 95/20 cent. (3x) | 46 | 250 | 62 |

*Nyacol ™ Zr series.

Centrifugation, removal of the supernatant, and re-dispersion of the colloidal $ZrO_2$ starting material results in increases in the average pore diameter, pore volume and surface area of fired spherules. This increase is believed to result from the removal of small (ca. 5-10 nm) colloidal $ZrO_2$ particles which are known to be present in the Nyacol ™ Zr series sols as a minor component. Many of these smaller $ZrO_2$ particles remain suspended during centrifugation and are removed when the supernatant is discarded prior to re-dispersion of the larger sedimented $ZrO_2$ particles. If present, these small $ZrO_2$ particles are believed to increase the packing density of the spherules by filling the interstices between larger $ZrO_2$ particles and therefore decreasing the average pore diameter, pore volume and surface area of the fired spherules.

It is also possible that sedimentation by centrifugation may result in agglomeration of the colloidal $ZrO_2$ particles into aggregates which pack together in a more open structure (effectively behaving as larger particles) than unaggregated particles.

Regardless of mechanism, the centrifugation treatments described in Examples 6-8 provide a method of preparing spherules with increased average pore diameter, pore volume and surface area relative to spherules prepared from untreated colloidal $ZrO_2$ sols.

The following example demonstrates the use of the unmodified $ZrO_2$ spherules prepared as described above in the chromatographic separation of proteins.

EXAMPLE 9

Protein Separation $ZrO_2$ spherules prepared as described in Example 2 were heated to 600° C. for 6 hrs. The spherules were classified and the 5-10μ fraction was used. The surface area of the spherules was 55 $m^2/g$ and the average pore diameter was 146 Å. The $ZrO_2$ spherules were slurried in methanol and packed into a 30×0.46 cm stainless steel column at a constant pressure of 4,000 p.s.i. to rapidly compress the $ZrO_2$/methanol slurry to yield a uniform packing. After packing, the flow was maintained at 1 ml/min. at 1,000 p.s.i. The column was washed with 150 ml of 100 mM sodium phosphate, pH 7.0. All subsequent chromatography was performed in phosphate buffer. The column was stored in 20% methanol/water.

Protein solutions (2 mg/ml) were prepared in the same phosphate buffer: 20 µl samples of bacitracin, 1.4 KDa; ovalbumin, 45 KDa; and bovine serum albumin (67 KDa) samples were injected and eluted with 30 ml of buffer. All chromatographic runs were performed with a Spectra Physics Model 8700XR HPLC system with their Model 757 variable wavelength detector set at 280 nm. Elution profiles, peak areas and elution volumes were recorded on a Model 4290 integrator/recorder. The proteins eluted as shown in Table IV, below, consistent with results expected in exclusion chromatography.

TABLE IV

| Protein | Elution Volume (ml) |
|---|---|
| Bacitracin | 3.35 |
| Ovalbumin | 2.51 |
| Bovine Serum Albumin | 2.38 |

EXAMPLE 10

Protein Separation $ZrO_2$ spherules prepared as described in Example 2 were heated to 600° C. for 6 hrs. Particles in the 30–50µ diameter range having a surface area of 30 m$^2$/g and an average pore diameter of 100 Å were used. The spherules were hand-packed into a 5 cm×0.21 cm column via a methanol slurry. After packing, the column was washed for 12 hrs at 0.2 ml/min. with pH 7.0, 50 mM phosphate buffer. All subsequent chromatography was done on an IBM 9533 LC at a flow rate of 1 ml/min. and used a pH gradient of 50 mM $H_3PO_4$ at pH 2.0 to 50 mM $Na_2HPO_4$ at pH 10 over a time of 10 min., followed by an additional 10 min. of isocratic operation at pH 10 with 50 mM $Na_2HPO_4$. Bovine serum albumin (BSA) and myoglobin were separated by adsorption and ion exchange chromatography, yielding retention times of 13.3 min. (BSA) and 17.8 min. (myoglobin).

EXAMPLE 11

Anion Exchange Chromatography

A stationary phase suitable for anion exchange chromatography was prepared by adsorption of polyethyleneimine [Polysciences, Inc., Warrington, Pa.] and subsequent cross-linking with 1,4-butanediol digylcidyl ether (95%, Aldrich Chemical Co., Milwaukee, Wis.); by the method of Regnier et al., *J. Chromatoq.*, 185, 375 (1979); 318, 157 (1985); 359, 121 (1986).

The anion exchange capacity for adsorption of picric acid was determined to be 230 µmoles/g of modified $ZrO_2$. This substrate was used to separate ovalbumin from BSA. The column was operated with a gradient of 10 mM Tris buffer at pH 7.5 to 10 mM Tris at pH 7.5 with 0.5M NaCl over 20 min., followed by an additional 10 min. of isocratic operation at pH 7.5 with 0.5M NaCl. The flow rate was 1 ml/min. The retention times were 9.75 (ovalbumin) and 22.8 min. (BSA).

The following example demonstrates the use of the $ZrO_2$ spherules to immobilize proteins.

EXAMPLE 12

Protein Immobilization $ZrO_2$ spherules with a diameter of approximately 30µ and a surface area of 50 m$^2$/g and an average pore diameter of 124 Å were used. Mouse antihuman IgE antibody was purified and radioiodinated ($I^{125}$) by the method of S. M. Burchiel et al., *J. Immunol. Meth.*, 69, 33 (1984); K. L. Holmes et al., *PNAS USA*, 82, 7706 (1985), and diluted with unlabelled antibody to yield a specific radioactivity of 5,000 cpm/µg. A portion of 250 µl of antibody (250 µg/ml in 5 mM Tris, pH 8.0) was added to tubes containing 10 mg of spherules. The mixture was briefly evacuated, then rocked at ambient temperature for the appropriate time, 5–120 min., with three replicates for each time point. The tubes were centrifuged and rinsed twice with 1 ml of buffer. The spherules were transferred to a fresh tube along with 2 ml of buffer, the buffer removed and the radioactivity of each tube was determined in a Packard Model 5230 gamma scintillation counter. The amount of bound protein in ng, converted from cpm, is shown in Table V.

TABLE V

| Time (Min.) | Antibody Bound/mg Spherules |
|---|---|
| 10 | 54 ng |
| 20 | 66 ng |
| 30 | 72 ng |
| 60 | 69 ng |
| 120 | 62 ng |

EXAMPLE 13

Extent of Binding of Monoclonal Antibodies

Using the same materials and techniques described in Example 12, the extent of binding of mouse antihuman IgE antibody in 2 hr incubations as a function of its concentration (1–250 µg/ml) was determined. The averages of three replicates show a saturation (Table VI). Double-reciprocal analysis of these data extrapolate to 100 µg antibody bound per g spherule at saturation.

TABLE VI

| Conc. Protein (µg/ml) | Antibody Bound/mg Spherules |
|---|---|
| 1 | 1.5 ng |
| 5 | 7.5 ng |
| 10 | 14.0 ng |
| 50 | 38.0 ng |
| 250 | 62.0 ng |

EXAMPLE 14

A. Trypsin Immobilization

Solutions (2 mg/ml) of trypsin, a 24 KDa proteolytic enzyme and bovine serum albumin (BSA), a 67 KDa protein, were bound to 70 mg of the $ZrO_2$ spherules (average pore diameter 100 Å, surface area of 30 m$^2$/g) in 5 mM tris, pH 8.0 by agitating the degassed spherules in 1.0 ml of buffer for 17.5 hrs. Trypsin (15.3 mg) and 0.2 mg (BSA) bound per g of spherule, a proportion which might be expected from their relative sizes and the size of the pores.

Trypsin was assayed using the thioesterase assay disclosed by P. L. Coleman et al., *Meth. Enzymol.*, 80, 408 (1981). The bound spherules were suspended in 1 ml of buffer and a 5 µl aliquot was added to a tube containing 1.0 ml of substrate. After 2.5 min. of continuous shaking, a citrate-soybean trypsin inhibitor (STI) solution was added to quench the reaction. It was rapidly centrifuged and the supernatant removed for determination of the absorbance (A) at 412 nm. Assays were performed with the trypsin inhibitor in the substrate solution to determine whether it was able to inhibit the bound trypsin. The results of these assays are summarized on Table VII, below.

TABLE VII

| Sample | Trypsin Activity (A at 412 nm) | |
| --- | --- | --- |
| | −STI | +STI |
| Trypsin spherules | 2.36 | 1.79 |
| BSA spherules | 0.10 | 0.13 |
| Trypsin supernatant | 0.19 | 0.12 |

The results shown in Table VII indicate that about 75% of the bound activity is unavailable to STI, even though STI is smaller than trypsin. In addition, only 4% of the activity is attributable to unbound trypsin, a surprisingly low value given the inefficient batch washing method which was used.

Calculations based on these observations demonstrated several unexpected results. Foe example, 15 mg of trypsin/g $ZrO_2$ corresponds to 51 mg/ml using 3.3 g/ml as the density of the spherules. This corresponds to a trypsin concentration of 2 mM in the column. A check on this may be made by estimating the expected absorbance at 412 nM for the assay. In these assays, the spherule-bound enzyme was 0.21 $\mu$M, the kcat for the substrate is 75/sec [G. D. J. Green et al., *Anal. Biochem.*, 93, 223 (1979)] and the extinction coefficient is 14,100, yielding an estimated 3.3 absorbance change, which compares favorably with the 2.4 observed. Since chromogen was present in amount sufficient to give only 2.8 A at 412 nm, it is safe to assume that nearly all of the bound trypsin is active. Thus, an extraordinary amount of protein is bound and retains its enzymic activity.

B. Chymotrypsinogen-Chymopapain-BSA Immobilization

The procedure of Example 8 (triple centrifugation) was employed to prepare $ZrO_2$ spherules having 240 Å pores and a surface area of 27 m$^2$/g. Small columns were poured, each containing about 1.0 g of spherules, and were equilibrated with either 20 mM tris-chloride buffer (pH 8.0) or 50 mM sodium acetate buffer (pH 4.5). Chymotrypsinogen (24.5 kDa) and chymopapain (32 kDa) were dissolved in the tris buffer and BSA was dissolved in the acetate buffer. Protein-containing solution was continuously added to the column until the 280 nm absorbance of the eluate equalled that of the starting solution. Unbound protein was rinsed from the column, and the amount of bound protein was calculated from the difference between that added and that recovered in the eluate.

Chymotrypsinogen and chymopapain bound at 76.9 mg and 24.5 mg of protein/g of spherules at pH 8.0, respectively, and 64 mg of BSA bound per gram of spherules at pH 7.5. Converting these values into binding densities per ml of column volume yields 254, 81 and 211 mg/ml of protein, respectively.

The fact that at acidic pH, albumin binds to a greater extent than does the smaller chymopapain, and almost to the extent as the event smaller chymotrypsinogen suggests that the latter enzymes would bind to even greater densities at lower pH, i.e., below their pIs.

EXAMPLE 15

Phosphoric Acid Treatment of $ZrO_2$ Particles

The following experiment was performed in order to determine the extent of reaction between phosphoric acid and $ZrO_2$ particles as a function of concentration, temperature and time. The $ZrO_2$ particles were prepared by a procedure similar to that described in Example 5, Preparation A, with the exception that they were fired to a temperature of 400° C. rather than 600° C. The resulting particles were about 100–400 $\mu$ in size, and had a surface area of about 117 m$^2$/g. Since no chromatographic evaluation of the particles prepared in this experiment was planned, these irregularly shaped particles were used, rather than spherules. Since the particles were prepared using the same raw materials and process as the spherules of Example 5A, the particles possess the same pore structure as the spherules of Example 5A.

Sixteen samples of particles were treated according to the combinations of concentration, time, and temperature shown in Table VIII, below. For each treatment condition, a 5.0 g portion of the particles was placed in a filter flask and 200 g of phosphoric acid solution at the concentrations indicated in Table VIII was added to the flask. The flask was then evacuated to remove air from the pores and to allow the acid solutions to wet the pores. The vacuum was then released and the flask maintained at the temperature indicated in Table VI for the indicated time period. A total of 16 samples were treated; eigth of the samples at 25° C., and the other eight at 100° C. Within each group of eight samples, half of the samples were treated for one hour at the temperature indicated; the other half were treated for four hours.

Following the phosphoric acid treatment, all samples were collected on a filter paper and the particles washed thoroughly with distilled water. Following drying for 24 hours at 80° C. and examination under an optical microscope, the particles were observed to be intact and crack-free. The surface area of each sample of particles was determined by nitrogen adsorption. The wt-% phosphate in each sample of treated particles was determined by dissolving a portion of each sample of the particles in hydrofluoric acid (HF) and analyzing the solutions by Inductively Coupled Plasma Spectroscopy (ICP). From the wt-% of phosphorus obtained from ICP, the wt-% of phosphate was calculated by assuming all of the phosphorus to be in the form of $PO_4$ ions, as described above. The results of these analyses are shown in Table VIII, below.

TABLE VIII

| | Results of Phosphoric Acid Treatment | | | | | |
| --- | --- | --- | --- | --- | --- | --- |
| Sample # | $H_3PO_4$ Conc. (moles/kg) | Temp. (C.) | Time (hrs) | S.A. m$^2$/g | $PO_4$ wt % | P/Zr (molar) |
| 1 | 0.00 | 25 | 1 | 116 | 0.27 | 0.004 |
| 2 | 0.01 | 25 | 1 | 115 | 2.44 | 0.032 |
| 3 | 0.10 | 25 | 1 | 104 | 4.28 | 0.057 |
| 4 | 1.00 | 25 | 1 | 110 | 4.77 | 0.063 |
| 5 | 0.00 | 25 | 4 | 113 | 0.27 | 0.004 |
| 6 | 0.01 | 25 | 4 | 116 | 2.63 | 0.034 |
| 7 | 0.10 | 25 | 4 | 121 | 4.65 | 0.061 |
| 8 | 1.00 | 25 | 4 | 117 | 4.77 | 0.065 |
| 9 | 0.00 | 100 | 1 | 124 | 0.27 | 0.004 |
| 10 | 0.01 | 100 | 1 | 124 | 2.48 | 0.032 |
| 11 | 0.10 | 100 | 1 | 114 | 5.20 | 0.070 |
| 12 | 1.00 | 100 | .1 | 109 | 7.47 | 0.101 |
| 13 | 0.00 | 100 | 4 | 105 | 0.31 | 0.004 |
| 14 | 0.01 | 100 | 4 | 110 | 3.46 | 0.045 |
| 15 | 0.10 | 100 | 4 | 117 | 6.82 | 0.089 |
| 16 | 1.00 | 100 | 4 | 111 | 10.25 | 0.149 |

The results shown in Table VIII indicate that the surface area (S.A.) of the particles was not greatly or systematically affected by the treatments described. The results also indicate that the amount of phosphate incorporated in the particles increased for a given temperature and time with increasing $H_3PO_4$ concentration. For a given $H_3PO_4$ concentration, the amount of phosphate (as calculated from phosphorous wt-%) incorporated into the particles increased with increasing treatment temperature and time. On samples treated at 25° C., however, the phosphorous content of the particles was only slightly greater after a treatment time of four hours than after a treatment time of one hour for a given $H_3PO_4$ concentration.

EXAMPLE 16

Mechanical and Physical Characterization of Phosphoric Acid Treated Spherules

The following experiment was performed in order to determine the effect of treating $ZrO_2$ spherules with an inorganic phosphate after rigorous pretreatment of the spherules with acid and base solutions.

$ZrO_2$ spherules were prepared according to Example 5, Preparation B, above. Fifteen g of the spherules were slurried in 200 ml of 0.5M HCl and thoroughly degassed by sonication and application of a vacuum. After one hour, during which the spherules were re-suspended three times by shaking, the HCl was decanted and the spherules rinsed five times with freshly boiled and cooled deionized water. This procedure was then repeated substituting 0.5M NaOH for the 0.5M HCl. The rinsed spherules were placed in a 250 ml round bottomed flask, to which 200 ml of an aqueous solution of 0.10M phosphoric acid in 1.0M KCl was added. The slurry was refluxed at about 100° C. for four hours. The flask was swirled several times during this period to insure that the particles remained suspended. After four hours of refluxing, the supernatant was decanted and the particles thoroughly rinsed with freshly boiled and cooled deionized water.

The surface areas of the untreated and $H_3PO_4$ treated spherules were measured to be 12.4 and 14.7 $m^2/g$, respectively.

In order to test their mechanical stability, the $H_3PO_4$ treated spherules were packed into a $50 \times 4.6$ mm i.d. HPLC column from a slurry of isopropanol, using an upward slurry packing technique at 4500 p.s.i. The spherules did not appear to have suffered any loss of mechanical stability due to the phosphating process, as evidenced by the fact that no fines developed during the packing procedure to clog the column frit. During almost daily use of the column over a three-month period, the column back pressure remained at about 200-300 p.s.i., providing further evidence of the stability of the phosphate treated spherules.

All chromatographic studies in these experiments were performed using an IBM Instruments 9533 Ternary Chromatograph with an IBM Instruments 9522 UV absorbance detector. Data were acquired using an IBM Instruments Series 9000 laboratory computer with the Chromatography Applications Program (CAP) software or a Hewlett-Packard 3393A Integrator. All proteins to be chromatographically separated were obtained from Sigma Chemical Co. (St. Louis, Missouri) and were used without further purification.

The loading capacity of the HPLC column packed with $H_3PO_4$ treated spherules was investigated chromatographically using lysozyme at three different injection concentrations. The spherules were prepared according to Example 5, Preparation A and treated with $H_3PO_4$ as described above (100° C. for four hours), and had an average diameter of 5 $\mu$ and average pore size of 100Å. In each of the three chromatographic studies, lysozyme was eluted using a 30 minute linear gradient from 50 mM potassium phosphate at pH 7.00 to 0.5M potassium phosphate at pH 7.00, with a flow rate of 1 ml/min. The area to height ratio was used as an indication of column performance. Table IX below lists the results of these studies.

TABLE IX

Column Loading Studies

| Amount of Lysozyme | Area/Height Ratio |
| --- | --- |
| 3 $\mu$g | 14.53 |
| 150 $\mu$g | 15.20 |
| 1.5 mg | 29.74 |

As shown by the data of Table IX, the area/height ratio at 1.5 mg of lysozyme is nerly twice that at 150 $\mu$g of lysozyme, indicating the column capacity lies between these two loading amounts.

Additional studies were performed to determine whether lysozyme retained any significant enzymatic activity after being retained on the column packed with the $H_3PO_4$ treated $ZrO_2$ spherules. The lysozyme activity assay was performed according to procedures developed by the Technical Assistance Department of Sigma Chemical Company, St. Louis, Missouri. Total protein was determined by the BCA total protein assay, according to Smith et al., *Anal. Biochem.*, 150, 76–85 (1985). A reagent kit available from Pierce Chemical Company, Rockford, Illinois, was utilized in the assay. Lysozyme was used for the calibration standards. The assay results showed that the specific enzymatic activity of the lysozyme was retained.

EXAMPLE 17

Protein Separation

Inorganic phosphate-treated $ZrO_2$ spherules were tested for their ability to separate large biomolecules such as proteins. Spherules having an average diameter of 20 $\mu$ and an average pore diameter of 408Å were prepared according to Example 5, Preparation B, and were treated with $H_3PO_4$ following the procedure and conditions described in Example 16. The treated spherules were packed into a $50 \times 4.6$ mm HPLC column. A test mixture of cytochrome-c, ribonuclease A, and lysozyme was chromatographically separated using a 30 minute linear gradient from 0.05M potassium phosphate at pH 7.00 to 0.5M potassium phosphate at pH 7.00. The results are depicted in FIG. 1. Bovine serum albumin (BSA) was unretained at the initial pH and phosphate concentration. The chromatogram of FIG. 1 indicates that the inorganic phosphate-treated $ZrO_2$ spherules are a useful support for protein separation.

EXAMPLE 18

Effect on Selectivity by Addition of Phosphate to Mobile Phase

Bovine Serum Albumin (BSA) is irreversibly retained in a 10 mM 2-[N-Morpholino]ethanesulfonic acid (MES) pH 6.00 buffered mobile phase, yet it is unretained upon addition of 1 mM phosphate to the mobile phase. In this experiment, the separation of a protein mixture of myoglobin, lysozyme, ribonuclease A and cytochrome C was attempted using a $50 \times 4.6$ mm chromatographic column packed with $ZrO_2$ spherules having an average pore diameter of 408Å, prepared according to Example 5, Preparation B. A 10 mM MES pH 6.00 buffered mobile phase and a 15 minute linear KCl elution gradient (0.00M KCl to 0.80M KCl) were utilized. No phosphate was present in the mobile phase. These conditions resulted in an almost total loss of selectivity.

The experiment was then repeated by adding 1.0 mM potassium phosphate to the mobile phase. The 50×4.6 mm column was packed with 20 μ spherule diameter, 408Å average pore diameter $ZrO_2$ spherules, prepared according to Example 5, Preparation B, and treated with $H_3PO_4$ according to the procedure and conditions of Example 16. The results depicted in FIG. 2 indicate that selectivity was mostly restored by the addition of the phosphate to the mobile phase, and demonstrate that phosphate ions played a critical role in the elution process of the proteins. It is possible that phosphate adsorbs onto the stationary phase from the mobile phase, modifying the phase and its retention properties.

EXAMPLE 19

Comparison of Inorganic Phosphate Treated $ZrO_2$ to Hydroxyapatite Supports

High performance hydroxyapatite ($Ca_{10}(PO_4)_6(OH)_2$) supports for HPLC separations of proteins have become commercially available. They are limited in several respects, however. The pressure limit of columns packed with the hydroxyapatite supports is at most 3000 psi (Regis Chemical Co., Morton Grove, Ill.), and the pH range operating range of the columns is generally from 5.5 to 10.5. Furthermore, all manufacturers note the need for guard pre-columns with these supports to prevent degradation of the main column. The guard columns must also be periodically replaced at considerable cost.

In the present studies, columns packed with inorganic phosphate-treated $ZrO_2$ according to Example 5, Preparation B, and Example 16 (procedure of second paragraph: HCL wash, NaOH wash, and phosphoric acid treatment) have been operated at pressures of up to 6000 p.s.i. Furthermore, the pH operating range limits of these columns are considerably wider than those of the hydroxyapatite supports. Additionally, the phosphate treated $ZrO_2$ column was used extensively without a guard column. When fouled, a sodium hydroxide rinse could be used to clean the column.

EXAMPLE 20

Separation of Monoclonal Antibodies

The purpose of this experiment was to determine whether the inorganic phosphate treated $ZrO_2$ spherules could be used to separate IgG monoclonal antibodies from a broth containing large amounts of albumin and some transferrin. $ZrO_2$ spherules prepared according to Example 5, Preparation B and treated with $H_3PO_4$ according to the procedures and conditions of Example 16, were used as the chromatographic support for a 50×4.6 mm column operated at a 30 minute linear gradient from 0.05M potassium phosphate at pH 6.0 to 0.5 potassium phosphate at pH 6.0. The mobile phase was a broth of the IgG monoclonal antibodies, bovine serum albumin (BSA) and transferrin. As shown in FIG. 3, antibodies were retained by the column. In this manner, it is believed that the inorganic phosphate treated $ZrO_2$ can be used in an initial cleanup step to retain antibodies, while the albumin and transferrin are passed through the column unretained.

EXAMPLE 21

Polymer Adsorption/Cross-linking

Preparation A—Heavily loaded $ZrO_2$

A solution of 0.55 g of polybutadiene (Aldrich Chemical Co., Milwaukee, Wis., m.w. 4500, Cat. No. 20-050-6) in 50 ml of pentane was added to 3.5 g of $ZrO_2$ spherules prepared as described in Example 2 (fired at 600° C. for 6 hrs; particle size=20–45 microns) which had been boiled in $CO_2$-free water to fully hydrate the surface and then dried at 125° C. The slurry was placed in an ultrasonic bath and a water aspirator vacuum applied. Dicumyl peroxide (DCP) (0.01 g) was then added and the slurry was again placed in an ultrasonic bath and a vacuum applied. The pentane was removed in vacuo and the material dried at 70° C. under vacuum. The material was then heated in a tube furnace to 200° C. for 2 hrs and then washed successively with pentane, toluene, methylene chloride, tetrahydrofuran, methanol and 0.1M sodium hydroxide. Elemental analysis of the coated spherules showed a carbon load of 7.7%. A duplicate sample was prepared in an identical fashion and had a carbon load of 7.5%. Because of the extremely heavy load of polybutadiene, the specific surface area of the porous spherules, as determined by a BET measurement, decreased from 50.4 to 4 $m^2/gm$.

Preparation B—Lightly loaded $ZrO_2$ 35 ml of a solution of 0.09 g of polybutadiene in pentane was added to 3.5 g of $ZrO_2$ spherules and the resultant slurry was placed in an ultrasonic bath and a water aspirator vacuum applied. Pentane (10 ml) containing 0.002 g of DCP was then added and the slurry was again placed in an ultrasonic bath and a vacuum applied. The slurry was then shaken for one hr and the supernatant removed by filtration. The material was then washed as described in Preparation A. Elemental analysis of the coated spherules showed 0.84% carbon, while the BET results showed a specific surface area of 38.7 $m^2/gm$. The decrease in specific surface area from 50.4 to 38.7 $m^2/gm$ is similar to the reduction in surface area which occurs upon silylation of typical inorganic supports.

Preparation C—Intermediate load

A solution of 0.27 g of PBD in 50 ml pentane was added to 3.0 g of $ZrO_2$ spherules (mean particle diameter 3.5 microns). The slurry was placed in an ultrasonic bath and a vacuum applied. 5.2 mg of DCP in 10 ml of pentane were then added. The methodology of Preparation A was then followed. Elemental analysis showed 2.7% carbon.

Figure 4:
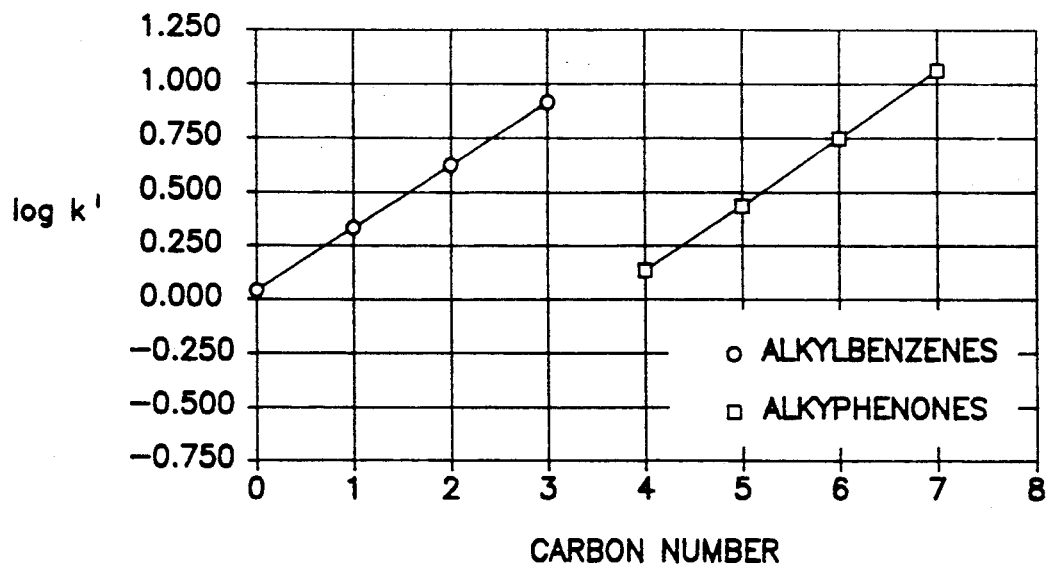
FIG. 4 is a schematic depiction of log k' (capacity factor) vs. carbon number for the members of homologous series of alkylphenones and alkylbenzenes, analyzed on a HPLC column packed with polybutadiene-loaded $ZrO_2$ spherules according to the present invention.

It is clear from the results of carbon analysis that carbon had been deposited on the surface of the $ZrO_2$ spherules. FIG. 4 further demonstrates the reversed-phase nature of the polymer-modified $ZrO_2$ spherules as exhibited by a 5 cm×0.46 cm column packed using Preparation C. The linearity of the log k' (capacity factor) vs. carbon number plot for the members of a homologous series of alkylphenones is clearly indicative of a reversed-phase retention mechanism.

EXAMPLE 22

Alteration of Selectivity

A mixed cation-exchange/reversed phase support was prepared by treating a material prepared as described in Example 21, Preparation C with a 100 mM aqueous $H_3PO_4$ solution at pH 3 for about one hour at 25° C. The retention data given in Table X show distinct changes in selectivity as a function of pH, volume fraction organic solvent and mobile phase ionic strength.

TABLE X

| Solute | Selectivity Factor* | | | | |
|---|---|---|---|---|---|
| | A | B | C | D | E |
| Butyl Benzene | 5.02 | 5.18 | 4.86 | 6.86 | 6.94 |
| Lidocaine | 0.28 | 0.074 | 0.1 | 0.44 | 0.32 |
| Quinine | 2.9 | 0.39 | 0.22 | 5.17 | 0.6 |
| Nortriptyline | 68.0 | 2.61 | 2.07 | 99.2 | 3.38 |
| Amitriptyline | 15.6 | 3.29 | 3.45 | 33.7 | 5.69 |

*Selectivity Factor = [k' (solute)]/[k'(toluene)]
Conditions and capacity factors of toluene are given below:
A = 60% MeOH/40% 10 mM PO4 at pH 7; k' (toluene) = 0.57
B = 60% meOH/40% 10 mM PO4 at pH 7 with 0.5M NaCl k' (toluene) = 0.54
C = 60% MeOH/40% 10 mM PO4 at pH 12; k' (toluene) = 0.58
D = 50% MeOH/50% 10 mM PO4 at pH 7; k' (toluene) = 1.2
E = 50% MeOH/50% 10 mM PO4 at pH 12; k' (toluene) = 1.2

Separations at high pH (above the pKa of the amines) are dominated by a reversed-phase retention mechanism as are separations at lower pH in high ionic strength mobile phase. Conversely, separations at low pH in a low ionic strength environment are controlled primarily by cation-exchange processes. In addition to the ability to alter selectivity in several ways, the subject material also exhibits dramatic improvement in terms of the peak symmetry of amine solutes relative to silica.

EXAMPLE 23 pH Stability Testing

The pH stability of the material of Example 21, Preparation A, was demonstrated in chromatographic experiments at high pH and elevated temperature by monitoring the retention of test solutes and by measurement of the amount of carbon on the support before and after prolonged exposure to high pH. These experiments were carried out under the following chromatographic conditions: Mobile Phase A: 0.1M $CO_2$-free NaOH; Mobile Phase B: Methanol; Flow Rate: 1 ml/min.; Oven Temp: 50° C.

Figure 5:
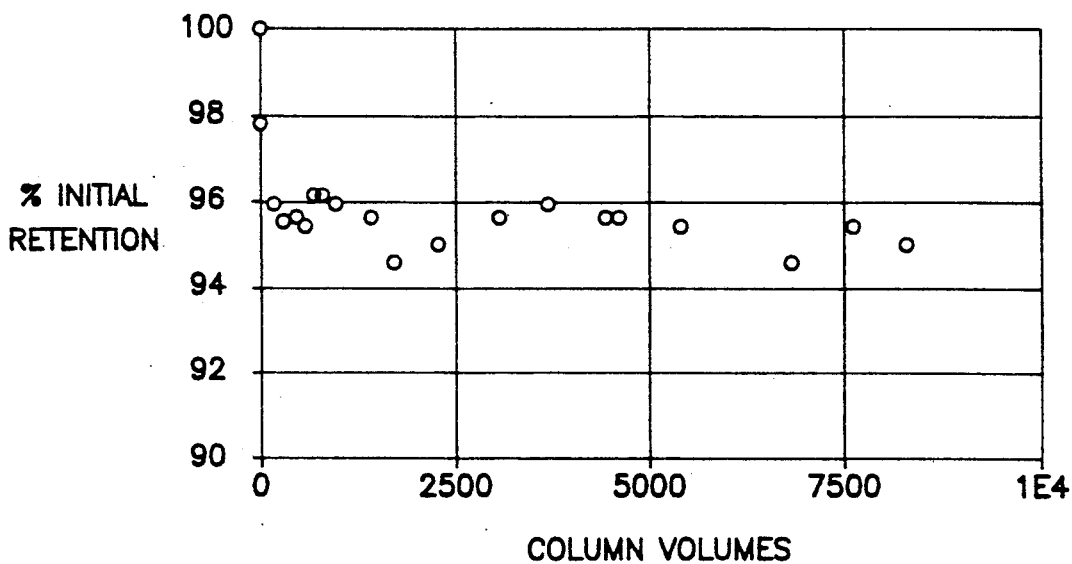
FIG. 5 is a schematic depiction of the percentage of initial retention of two test solutes in a mobile phase of 50% 0.1M $CO_2$-free NaOH and 50% methanol, as a function of the number of column volumes of mobile phase flushed through an HPLC column packed with polybutadiene-loaded $ZrO_2$ spherules (heavy loading of PBD) according to the present invention.
Figure 6:
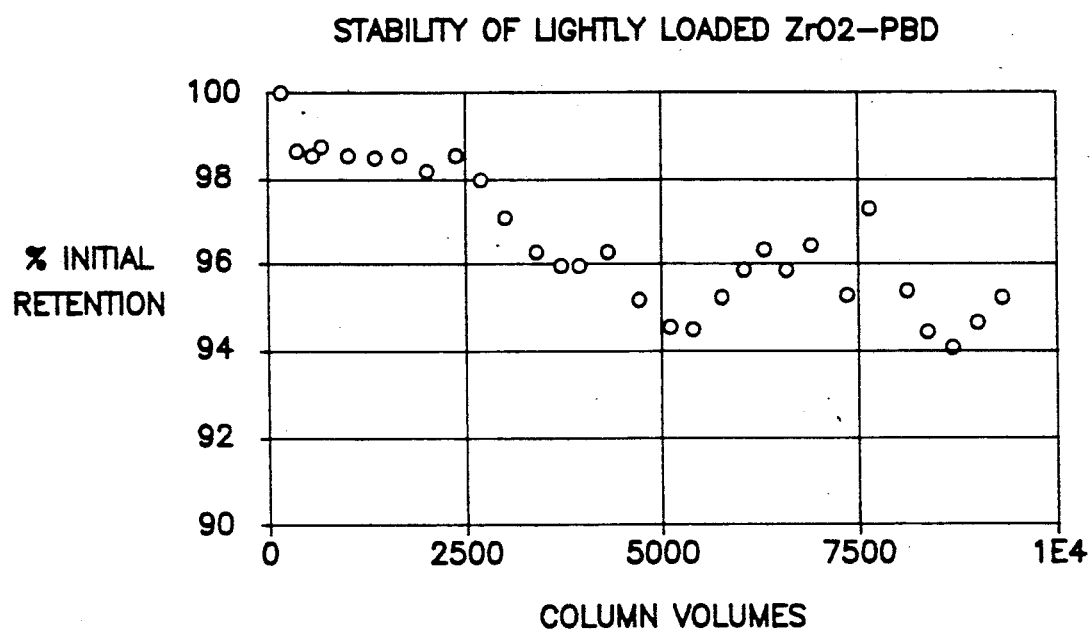
FIG. 6 is a schematic depiction of the percentage of initial retention of two test solutes in a mobile phase of 50% 0.1M $CO_2$-free NaOH and 50% methanol, as a function of the number of column volumes of mobile phase flushed through an HPLC column packed with polybutadiene-loaded $ZrO_2$ spherules (light loading of PBD) according to the present invention.

The retention of two test solutes in a mobile phase of 50% B/50% A as a function of the number of column volumes of mobile phase flushed through the column is shown in FIG. 5. Note that the initial decrease in retention reflects the equilibration of the column to the elevated temperature and not a loss in bonded phase. The evaluation was repeated on the lightly loaded material (Preparation B); the retention data on this material is shown in FIG. 6. Once again, there is an initial decrease in retention associated with column equilibration. There is also a slight decrease in retention at approximately 15 hours which accompanied a change in the lot of mobile phase; this change does not reflect a significant drop in carbon load.

It is believed that the above evaluations represent the most challenging test of pH stability which has been reported for any reversed-phase material and it is also believed that the data clearly show that the spherules of Example 22, Preparations A and B, are essentially stable under these conditions.

EXAMPLE 24

Allylphosphonate Treatment $ZrO_2$ spherules prepared by the procedure of Example 2 (3.4 g, surface area: 60 $m^2/g$; pore diameter: 95 Å) were treated with a solution of 1.6 g of allylphosphonic acid in 50 ml of 95/5 (v/v) methanol/water. After "ultrasonicating" under vacuum and shaking for one hr, the supernatant was removed by filtration and the phosphonate-treated $ZrO_2$ was dried at 70° C. for 12 hrs. The material was then modified with PBD according to Example 21, Preparation C. In this manner, the residual $ZrO_2$ surface was deactivated as is clearly shown by the data in Table XI, below. Note that carboxylic acids are not eluted on the non-phosphonated $ZrO_2$ material but are eluted on the phosphonated material.

TABLE XI

| Solute | k' (untreated) | k' (treated) |
|---|---|---|
| Toluene | 0.46 | 0.49 |
| Benzoic Acid | not eluted | 6.1 |

EXAMPLE 25

Regeneration of Column Retention Characteristics

Several 100 μl injections of cytochrome C were made on a column packed with material prepared as described in Example 21, Preparation C. The retention of cytochrome C on this material decreased due to "irreversible" adsorption of protein upon each injection.

The column was then "pulsed" with 5, 100 μl injections of 1M NaOH in order to strip the "irreversibly adsorbed" cytochrome C. The effect of the pulses is to strip the column of adsorbed protein such that the original retention characteristics can be regenerated.

EXAMPLE 26

Exposure to Sterilizing Conditions

A. Polybutadiene-Coated Spherules

The ability of the PBD-coated spherules to withstand sterilizing conditions was demonstrated by evaluation of the chromatographic characteristics of a sample of the spherules prepared as described in Example 21, Preparation C, before and after exposure of the sample to a mobile phase of 1M NaOH at 100° C. for 1 hr. As indicated by the data in Table XII below, there was no decrease in retention of nonpolar substances upon challenging the packing in this fashion.

TABLE XII

| Solute | k' Before Treatment | k' After Treatment |
|---|---|---|
| Benzene | 1.36 | 1.47 |
| Toluene | 2.68 | 3.01 |
| Ethyl Benzene | 4.83 | 5.57 |
| Propyl Benzene | 9.21 | 10.86 |

A second column (ES Industries, Marlton, N.J.), packed with an alumina support modified by the method of G. Shomberg, LC-GC, 6, 36 (1988), was challenged with a mobile phase of 1M NaOH, which was collected in two fractions. The first corresponded to an elution time of 1 hr and the second to an additional elution of 2.25 hrs.

The eluents were analyzed via an inductively coupled plasma spectrometer. The concentration of alumina in the eluent from the second column corresponded to the dissolution of a total of 10% of the mass of the alumina in the column.

In marked contrast, zirconium was absent in the eluent of the zirconium column at a level of detectability of 0.03 μg/ml. Even if Zr was present at the detection limit, this would correspond to loss of less than 0.001% of the mass of $ZrO_2$ on the test column.

B. Polystyrene-, Poly(t-butyl)styrene- and Polyisoprene-Coated Spherules

The ability of three additional polymer-coated phases to withstand the sterilizing conditions described above was also evaluated. The additional polymer coatings tested were polystyrene ("PS", 3850 m.w.), poly(t-butyl)styrene ("PTBS", 3930 m.w.), and polyisoprene ("PI", 3000 m.w.). The spherules coated with these additional polymers were prepared as follows:

1. Preparation of Polystyrene-Coated Spherules

Porous $ZrO_2$ spherules having a diameter from about 1 to 10μ, a surface area of 47.7 $m^2/g$, and an average pore diameter of about 118 Å were coated with polystyrene, a hydrophobic, aromatic polymer, as follows: 0.45 g of the oligomeric polystyrene (m.w. 3850) were dissolved in 200 ml of toluene. To this solution were added 10 ml of toluene in which 0.01 g of dicumyl peroxide initiator had been dissolved. The resulting solution was placed in a 1000 ml round bottom flask. 15.0 g of the $ZrO_2$ spherules were added to the flask before placement of the flask on a rotary evaporator and rotation under a pressure of 15 in. of Hg for about 15 mins. The pressure was then reduced to 26-28 in. of Hg, until the toluene was removed. Some agglomerating of the resulting spherules was observed.

After release of the vacuum, toluene was added to the flask to redissolve the oligimer and initiator. An additional 1.0 g of $ZrO_2$ spherules were added to the flask, and the toluene was removed under a vacuum of 26-28 in. of Hg. The resulting oligimer-coated spherules were not agglomerated, and the resulting batch flowed easily when poured.

The flask containing the spherules was then placed in a vacuum oven and was heated to a temperature of 170° C. under a vacuum of about 29-30 in. Hg for 4 hours, in order to cross-link the oligimeric polystyrene. After curing, analysis of a sample of these coated spherules indicated that the carbon and hydrogen content of the spherules were 1.7 wt-% and 0.3 wt-%, respectively. The polystyrene-coated spherules were then Soxhlet-extracted with toluene for 4 hours. Surface area analysis of the coated spherules indicated that their average surface area was 39.5 $m^2/g$, and the average pore diameter about 100 Å. The spherules were then classified on a Gilson Inc. sonic siever; spherules having diameters between 5 and 10μ were used to pack an HPLC column.

2. Preparation of Polyisoprene-Coated Spherules

A second sample of $ZrO_2$ spherules, having a diameter of 1-10μ and a surface area of 28 $m^2/g$, were coated with polyisoprene, an aliphatic, hydrophobic polymer. 0.2 g of the oligomeric polyisoprene (m.w. 3000) and 0.005 g of dicumyl peroxide initiator were dissolved in 300 ml of heptane. The resulting solution was placed in a 1000 ml round bottom flask. 10 g of $ZrO_2$ spherules were added to the flask, which was then placed on a rotary evaporator and rotated under a pressure of about 15 inches of Hg for about 15 minutes until the heptane was removed. The flask containing the spherules was then exposed to a vacuum of 29-30 in. of Hg for 2 hours in order to cross-link the polyisoprene. The spherules were then extracted with heptane for 4 hours in a Soxhlet extractor.

3. Preparation of Poly(t-butyl)styrene-Coated Spherules

A third sample of $ZrO_2$ spherules having a diameter from about 1 to 10μ, a surface area of 47.7 $m^2/g$, and an average pore diameter of about 118 Å were coated with poly(t-butyl)styrene, a hydrophobic polymer with both aliphatic and aromatic character. 0.4 g of the poly(t-butyl)styrene (3930 m.w.) was dissolved in 200 ml of toluene. To this was added a solution of 0.01 g of dicumyl peroxide dissolved in 10 ml of toluene. The resulting solution was placed in a 1000 ml round bottom flask, and 20.0 g of the $ZrO_2$ spherules were added. The flask was then placed on a rotary evaporator and rotated under a pressure of about 15 inches of Hg for about 15 minutes. The pressure was then reduced to about 26-28 inches of Hg with removal of the toluene over about 1 hour. The coated spherules were observed to be slightly agglomerated.

150 ml of toluene were then added to the flask, in order to redissolve the poly(t-butyl)styrene and the initiator. An additional 4.2 g of $ZrO_2$ spherules were added to the flask, and the toluene was removed on the rotary evaporator over about an hour under the previously described conditions. The coated spherules flowed easily and were not agglomerated.

The spherules were next placed in a ceramic tray and cross-linked in a vacuum oven at 170° C. for 4 hours. Analysis of the carbon and hydrogen content of the poly(t-butyl)styrene coated spherules indicated that these were 1.4 wt-% and 0.3 wt-%, respectively. Surface area analysis of the coated spherules indicated that the surface area was 33.5 $m^2/g$.

4. Exposure to Sterilizing Conditions

After coating and cross-linking as noted, a portion of each of the three samples of polymer-coated spherules were used to pack HPLC columns without further modification. The HPLC columns were prepared by packing each 5 cm×4.6 mm id 316 stainless steel column blank with a sample of spherules coated with polystyrene, poly(t-butyl)styrene, or polyisoprene. Each HPLC column was equipped with ¼ inch 316 SS Parker-Hanifan end fittings and ¼ inch×1/32 inch 2 μm titanium frits. The coated spherules were packed at 6000 p.s.i. from a methanolic slurry, using a downward slurry packing technique.

The stabilities of the polymer-coated zirconia materials were then evaluated under "sterilizing" conditions by exposing the columns to a mobile phase of 1.0M NaOH for 3.25 hours, at a flow rate of 1.0 ml/min, while the column was held at a temperature of 100° C. The effluents of all three columns were collected, and half of each effluent was filtered through 0.45 μm Teflon TM filter. Both fractions of each effluent were then evaluated by inductively coupled plasma spectroscopy (ICP), in order to determine levels of zirconia and other metals present in each sample. The limit of detection for the ICP analysis was 0.03 μg/ml for zirconium.

The results of the ICP analysis of the three additional polymer-coated zirconium samples are summarized in Table XIII below, which indicates that no detectable amount of zirconium was present in the effluent from any of the samples. Nor was any zirconium detected in the sodium hydroxide blank solution. Upon opening each of the columns following the alkaline treatment, no voids were observed in the packing.

TABLE XIII

Aluminum, Silicon, and Zirconium Levels in the Effluent of Polymer Coated $ZrO_2$ Columns Exposed to Sterilizing Conditions[a]

| Column | Al (μg/ml) | Si (μg/ml) | Zr (μg/ml) |
| --- | --- | --- | --- |
| PS/$ZrO_2$ | <0.13[b] | 0.99 | <0.03[b] |
| PTBS/$ZrO_2$ | <0.13[b] | 2.3 | <0.03[b] |
| Pl/$ZrO_2$ | <0.13[b] | 1.1 | <0.03[b] |
| NaOH blank | <0.13[b] | 0.2 | <0.03[b] |

[a] 1.0M NaOH at 100° C. for 3.25 hours
[b] indicates limit of detection under these conditions The data of Table XIII demonstrate that the application of other hydrophobic polymer coatings to the zirconia spherules resulted in phases which behaved similarly to the PBD/$ZrO_2$ described above. No measurable zirconia was leached from these materials during sterilizing sodium hydroxide treatment, in contrast with the significant loss of alumina from the alumina support, described above.

The invention has been described with reference to various specific and preferred embodiments and techniques. However, it should be understood that many variations and modifications may be made while remaining within the spirit and scope of the invention.

What is claimed is:

1. A porous $ZrO_2$ spherule having a diameter of about 0.5-500 microns, a surface area of about 1-200 m²/g, and a pore size of about 20-500 Å, wherein the spherule is substantially stable in an aqueous solution of a pH of about 1-14, and wherein the spherule further comprises a surface incorporating a surface adsorbed phosphate in an amount effective to impart cation-exchange characteristics to the spherule.

2. The spherule of claim 1 which comprises about 0.5-15.0 wt-% phosphate.

3. The spherule of claim 2 which comprises about 2.0-12.0 wt-% phosphate.

4. The spherule of claim 1 which comprises a surface-adsorbed inorganic phosphate.

5. The spherule of claim 4 wherein the inorganic phosphate is derived from phosphoric acid or an alkali metal phosphate salt.

6. A porous $ZrO_2$ spherule having a diameter of about 0.5-500 microns, a surface area of about 1-200 m²/g, and a pore size of about 20-500 Å,
    (i) wherein the spherule is substantially stable in an aqueous solution of a pH of about 1-14;
    (ii) wherein the spherule further comprises a surface incorporating phosphate in an amount effective to impart cation-exchange characteristics to the spherule; and
    (iii) wherein said spherule further comprising said surface incorporating a surface adsorbed phosphate is produced by treating the porous $ZrO_2$ spherule with an aqueous solution of an inorganic phosphate for a period of time and at a temperature which are effective to adsorb phosphate onto said surface.

7. The spherule of claim 6, wherein the inorganic phosphate is $H_3PO_4$.

8. The spherule of claim 6, wherein the temperature is about 20°-30° C.

9. The spherule of claim 6, wherein the concentration of the inorganic phosphate in the aqueous solution is about 0.01-1.00 molal.

10. The spherule of claim 6, wherein the period of time is about 1-4 hours.

11. The spherule of claim 10, wherein the period of time is about 3-4 hours.

* * * * *